United States Patent
Bothe et al.

(10) Patent No.: US 10,782,450 B2
(45) Date of Patent: *Sep. 22, 2020

(54) SOFT CONTACT LENSES WITH A LUBRICIOUS COATING COVALENTLY-ATTACHED THEREON

(71) Applicant: Alcon Inc., Fribourg (CH)

(72) Inventors: Harald Bothe, Niedernhausen (DE); Bernhard Seiferling, Goldbach (DE); Heike Arndt, Mömlingen (DE); Thomas Wasse, Wörth (DE); Stephan Wittmar, Erlenbach (DE)

(73) Assignee: Alcon Inc., Fribourg (CH)

( * ) Notice: Subject to any disclaimer, the term of this patent is extended or adjusted under 35 U.S.C. 154(b) by 428 days.

This patent is subject to a terminal disclaimer.

(21) Appl. No.: 15/792,806

(22) Filed: Oct. 25, 2017

(65) Prior Publication Data

US 2018/0113236 A1 Apr. 26, 2018

Related U.S. Application Data

(60) Provisional application No. 62/412,925, filed on Oct. 26, 2016.

(51) Int. Cl.
| | | |
|---|---|---|
| *G02B 1/04* | (2006.01) | |
| *G02C 7/04* | (2006.01) | |
| *C08L 29/04* | (2006.01) | |
| *C07H 3/02* | (2006.01) | |
| *C07H 3/04* | (2006.01) | |
| *C08L 39/04* | (2006.01) | |
| *C08L 71/08* | (2006.01) | |
| *C09D 129/14* | (2006.01) | |
| *C08F 216/38* | (2006.01) | |
| *C08F 222/38* | (2006.01) | |
| *C08F 226/06* | (2006.01) | |
| *C08K 5/15* | (2006.01) | |

(52) U.S. Cl.
CPC ............ *G02B 1/043* (2013.01); *C07H 3/02* (2013.01); *C07H 3/04* (2013.01); *C08L 29/04* (2013.01); *C08L 39/04* (2013.01); *C08L 71/08* (2013.01); *C09D 129/14* (2013.01); *G02C 7/049* (2013.01); *C08F 216/38* (2013.01); *C08F 222/38* (2013.01); *C08F 226/06* (2013.01); *C08K 5/15* (2013.01)

(58) Field of Classification Search
None
See application file for complete search history.

(56) References Cited

U.S. PATENT DOCUMENTS

| | | | |
|---|---|---|---|
| 3,408,429 A | 10/1968 | Otto | |
| 4,347,198 A | 8/1982 | Ohkada et al. | |
| 5,461,433 A | 10/1995 | Nakabayashi et al. | |
| 5,508,317 A | 4/1996 | Muller | |
| 5,583,163 A | 12/1996 | Muller | |
| 5,741,923 A | 4/1998 | Driver et al. | |
| 5,789,464 A | 8/1998 | Muller | |
| 5,849,810 A | 12/1998 | Muller | |
| 6,218,508 B1 | 4/2001 | Kragh et al. | |
| 6,303,687 B1 | 10/2001 | Muller | |
| 6,627,124 B1 | 9/2003 | Herbrechtsmeier et al. | |
| 6,800,225 B1 | 10/2004 | Hagmann et al. | |
| 7,384,590 B2 | 6/2008 | Kelly et al. | |
| 7,387,759 B2 | 6/2008 | Kelly et al. | |
| 8,088,313 B2 | 1/2012 | Hagmann et al. | |
| 8,236,873 B2 * | 8/2012 | Suda .................. A61F 2/16 351/159.02 | |
| 8,529,057 B2 | 9/2013 | Qiu et al. | |
| 10,449,739 B2 * | 10/2019 | Qiu .................. B29D 11/00067 | |
| 2009/0156741 A1 | 6/2009 | Suda et al. | |
| 2012/0026457 A1 | 2/2012 | Qiu et al. | |
| 2012/0026458 A1 | 2/2012 | Qiu et al. | |
| 2012/0314185 A1 | 12/2012 | Bauman et al. | |
| 2013/0118127 A1 | 5/2013 | Kolluru et al. | |
| 2013/0337160 A1 | 12/2013 | Holland et al. | |
| 2016/0061995 A1 | 3/2016 | Chang et al. | |
| 2016/0326046 A1 | 11/2016 | Quinter et al. | |
| 2017/0068018 A1 | 3/2017 | Qian et al. | |
| 2017/0068019 A1 | 3/2017 | Qian et al. | |
| 2017/0165932 A1 | 6/2017 | Qian et al. | |
| 2018/0079157 A1 | 3/2018 | Tucker et al. | |
| 2018/0079158 A1 | 3/2018 | Qiu et al. | |
| 2018/0079889 A1 | 3/2018 | Chiang et al. | |
| 2018/0081197 A1 | 3/2018 | Qiu et al. | |

FOREIGN PATENT DOCUMENTS

| | | |
|---|---|---|
| EP | 0189375 A2 | 7/1986 |
| EP | 1465931 B1 | 8/2007 |
| WO | 02/071106 A1 | 9/2002 |
| WO | 2016/145204 A1 | 9/2016 |

* cited by examiner

*Primary Examiner* — Tae H Yoon
(74) *Attorney, Agent, or Firm* — Jian Zhou

(57) ABSTRACT

The invention is generally related to soft contact lenses which comprise a polyvinylalcohol-based hydrogel lens body and a durable lubricious coating thereon which are covalently attached to the polyvinylalcohol-based hydrogel lens body through 6-membered acetal rings and to a method for producing the same.

20 Claims, No Drawings

SOFT CONTACT LENSES WITH A LUBRICIOUS COATING COVALENTLY-ATTACHED THEREON

This application claims the benefit under 35 USC § 119 (e) of U.S. provisional application No. 62/412,925 filed 26 Oct. 2016, incorporated by reference in its entirety.

This invention is related to polyvinylalcohol-based (i.e., PVA-based) contact lenses each of which has a lubricious coating chemically attached onto the lens surface. In addition, the invention provides a method for making such contact lenses.

BACKGROUND

Most commercially-available non-silicone hydrogel contact lenses are produced according to a conventional cast molding technique involving use of disposable plastic molds and a mixture of vinylic monomers and crosslinking agents. There are several disadvantages with the conventional cast-molding technique. For example, a traditional cast-molding manufacturing process often includes lens extraction in which unpolymerized monomers must be removed from the lenses by using an organic solvent. Use of organic solvents can be costly and is not environmentally friendly. In addition, disposable plastic molds inherently have unavoidable dimensional variations, because, during injection-molding of plastic molds, fluctuations in the dimensions of molds can occur as a result of fluctuations in the production process (temperatures, pressures, material properties), and also because the resultant molds may undergo non-uniformly shrinking after the injection molding. These dimensional changes in the mold may lead to fluctuations in the parameters of contact lenses to be produced (peak refractive index, diameter, basic curve, central thickness etc.) and to a low fidelity in duplicating complex lens design.

The above described disadvantages encountered in a conventional cast-molding technique can be overcome by using the so-called Lightstream Technology™ (Alcon), which involves (1) a lens-forming composition being substantially free of monomers and comprising a substantially-purified, water-soluble polyvinylalcohol prepolymer with ethylenically-unsaturated groups, (2) reusable molds produced in high precision, and (3) curing under a spatial limitation of actinic radiation (e.g., UV), as described in U.S. Pat. Nos. 5,508,317, 5,583,163, 5,789,464, 5,849,810, 6,800,225, and 8,088,313. Non-silicone hydrogel Lenses produced according to the Lightstream Technology™, for example, DAILIES® AquaComfort Plus®, can have high consistency and high fidelity to the original lens design, because of use of reusable, high precision molds. In addition, contact lenses with high optical quality can be produced at relatively lower cost due to the short curing time, a high production yield, and free of lens extraction and in an environmentally friendly manner because of use of water as solvent for preparing lens formulations. However, although DAILIES® AquaComfort Plus® lenses have a good optical quality and a good surface wettability, they may not have a desired surface lubricity for ensuring a superior wearing comfort.

Therefore, there are still needs for a new non-silicone hydrogel contact lens having a superior surface lubricity and for a method capable of producing such contact lenses.

SUMMARY

In one aspect, the invention provides a method for producing soft contact lenses, comprising the steps of: (1) obtaining a preformed polyvinylalcohol-based hydrogel contact lens, wherein the preformed polyvinylalcohol-based hydrogel contact lens is composed of a polymer comprising at least 50% by mole of repeating units of vinyl alcohol; (2) contacting the preformed polyvinylalcohol-based hydrogel contact lens with a first aqueous coating solution of a hydrophilic polymer having reactive groups of

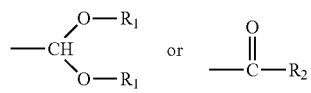

in which $R_1$ is methyl or ethyl and $R_2$ is hydrogen or a $C_1$-$C_4$ alkyl, at a pH of about 4.0 or less for a time period to covalently attach a layer (or coating) of the hydrophilic polymer onto the preformed polyvinylalcohol-based hydrogel contact lens through 6-membered acetal rings.

In another aspect, the invention provides a soft contact lens which comprises a polyvinylalcohol-based hydrogel lens body and a coating thereon, wherein the polyvinylalcohol-based hydrogel lens body is composed of a polymer comprising at least 50% by mole of repeating units of vinyl alcohol, wherein the coating is covalently attached onto the polyvinylalcohol-based hydrogel lens body through 6-membered acetal rings, wherein the soft contact lens has a surface lubricity better than the lubricity of the polyvinylalcohol-based hydrogel lens body.

DETAILED DESCRIPTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

"About" as used herein in this application means that a number, which is referred to as "about", comprises the recited number plus or minus 1-10% of that recited number.

"Optional" or "optionally" means that the subsequently described event or circumstance can or cannot occur, and that the description includes instances where the event or circumstance occurs and instances where it does not.

A "contact Lens" refers to a structure that can be placed on or within a wearer's eye. A contact lens can correct, improve, or alter a user's eyesight, but that need not be the case.

A "soft contact lens" refers to a contact lens which has an elastic modulus (i.e., Young's modulus) of less than 2.5 MPa.

As used in this application, the term "hydrogel" or "hydrogel material" refers to a crosslinked polymeric material which is insoluble in water, but can hold at least 10 percent by weight of water in its three-dimensional polymer networks (i.e., polymer matrix) when it is fully hydrated.

A "vinylic monomer" refers to a compound that has one sole ethylenically-unsaturated group.

The term "soluble", in reference to a compound or material in a solvent, means that the compound or material can be dissolved in the solvent to give a solution with a concentration of at least about 0.1% by weight at room temperature (i.e., from about 20° C. to about 30° C.).

The term "insoluble", in reference to a compound or material in a solvent, means that the compound or material can be dissolved in the solvent to give a solution with a concentration of less than 0.005% by weight at room temperature (as defined above).

The term "ethylenically unsaturated group" is employed herein in a broad sense and is intended to encompass any groups containing at least one >C=C< group. Exemplary ethylenically unsaturated groups include without limitation (meth)acryloyl

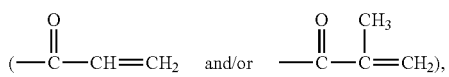

allyl, vinyl (—CH=CH$_2$), 1-methylethenyl

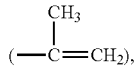

styrenyl, or the likes.

The term "(meth)acrylamide" refers to methacrylamide and/or acrylamide.

The term "(meth)acrylate" refers to methacrylate and/or acrylate.

A "hydrophilic vinylic monomer", as used herein, refers to a vinylic monomer which can be polymerized to form a homopolymer that is water-soluble or can absorb at least 10 percent by weight of water.

A "hydrophobic vinylic monomer" refers to a vinylic monomer which can be polymerized to form a homopolymer that is insoluble in water and can absorb less than 10 percent by weight of water.

As used in this application, the term "macromer" or "prepolymer" refers to a medium and high molecular weight compound or polymer that contains two or more ethylenically unsaturated groups. Medium and high molecular weight typically means average molecular weights greater than 700 Daltons.

As used in this application, the term "vinylic crosslinker" refers to a compound having at least two ethylenically unsaturated groups. A "vinylic crosslinking agent" refers to a vinylic crosslinker having a molecular weight of about 700 Daltons or less.

As used in this application, the term "polymer" means a material formed by polymerizing/crosslinking one or more monomers or macromers or prepolymers.

As used in this application, the term "molecular weight" of a polymeric material (including monomeric or macromeric materials) refers to the weight-average molecular weight unless otherwise specifically noted or unless testing conditions indicate otherwise.

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkyl triradical" refers to a trivalent radical obtained by removing two hydrogen atoms from an alkyl. A alkyl triradical forms three bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), C$_1$-C$_4$ alkyl, C$_1$-C$_4$ alkoxy, C$_1$-C$_4$ alkylthio (alkyl sulfide), C$_1$-C$_4$ acylamino, C$_1$-C$_4$ alkylamino, di-C$_1$-C$_4$ alkylamino, halogen atom (Br or Cl), and combinations thereof.

In this application, a "6-membered acetal ring" refers to a moiety of

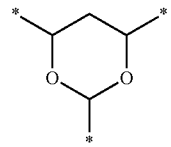 [SMILES: *C1CC(*)OC(*)O1]

which can be formed in an acid-catalyzed reaction between a 1,3-diol moiety

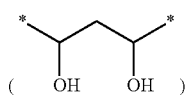

and a group of

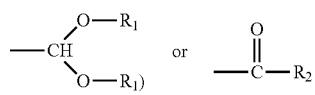

in which R$_1$ is methyl or ethyl and R$_2$ is hydrogen or a C$_1$-C$_4$ alkyl.

In this application the term "azetidinium" or "3-hydroxyazetidinium" refers to a positively-charged, divalent radical (or group or moiety) of

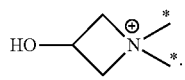

The term "azlactone" refers to a mono-valent radical of formula

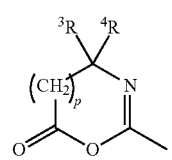

in which p is 0 or 1; $^3R$ and $^4R$ independently of each other is $C_1$-$C_8$ alkyl (preferably methyl).

As used in this application, the term "phosphorylcholine" refers to a monovalent zwitterionic group of

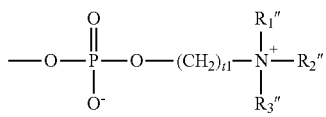

in which t1 is an integer of 1 to 5 and $R_1"$, $R_2"$ and $R_3"$ independently of one another are $C_1$-$C_8$ alkyl or $C_1$-$C_8$ hydroxyalkyl.

In this application, an "oxazoline" refers to a compound of

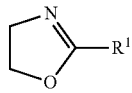

in which $R^1$ is hydrogen, $C_1$-$C_{18}$ alkyl, $C_1$-$C_4$ alkyl-substituted phenyl, $C_1$-$C_4$-alkoxy-substituted phenyl, $C_6$-$C_{18}$ aryl radical, N-pyrrolidonyl-$C_1$-$C_4$ alkyl, a monovalent radical of -alk-$(OC_2H_4)_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)), preferably R1 is methyl, ethyl, propyl, N-pyrrolidonyl-$C_1$-$C_4$ alkyl, a monovalent radical of -alk-$(OC_2H_4)_{m3}$—OR" (in which alk is $C_1$-$C_6$ alkyl diradical, R" is $C_1$-$C_4$ alkyl, preferably methyl, and m3 is an integer from 1 to 10 (preferably 1 to 5)).

In this application, the term "polyoxazoline" refers to a linear polymer having a formula of

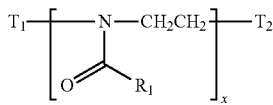

in which: T1 and T2 are two terminal groups; $R^1$ is hydrogen, methyl, ethyl, N-pyrrolidonylmethyl, N-pyrrolidonylethyl, N-pyrrolidonylpropyl, or a monovalent radical of -alk-$(OC_2H_4)_{m3}$—OR" in which alk is $C_1$-$C_4$ alkyl diradical; R" is $C_1$-$C_4$ alkyl (preferably methyl); m3 is an integer from 1 to 10 (preferably 1 to 5); x is an integer from 5 to 500. A polyoxazoline segment has a divalent polymer chain of a formula of

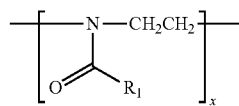

in which $R^1$ and x are as defined above.

In this application, the term "poly(2-oxazoline-co-ethyleneimine)" refers to a statistical copolymer having a formula of

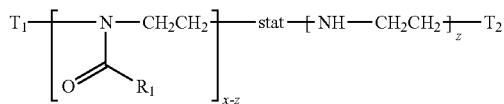

in which: T1 and T2 are terminal groups; $R^1$ is hydrogen, methyl, ethyl, N-pyrrolidonylmethyl, N-pyrrolidonylethyl, N-pyrrolidonylpropyl, or a monovalent radical of -alk-$(OC_2H_4)_{m3}$—OR" in which alk is $C_1$-$C_4$ alkyl diradical; R" is $C_1$-$C_4$ alkyl (preferably methyl); m3 is an integer from 1 to 10 (preferably 1 to 5); x is an integer from 5 to 500; z is an integer equal to or less than x. A poly(2-oxazoline-co-ethyleneimine) is obtained by hydrolyzing a polyoxazoline.

In this application, the term "poly(2-oxazoline-co-ethyleneimine)-epichlorohydrin" refers to a polymer obtained by reacting a poly(2-oxazoline-co-ethyleneimine) with epichlorohydrin to convert all or substantial percentage (≥90%) of the secondary amine groups of the poly(2-oxazoline-co-ethyleneimine) into azetidinium groups. Examples of poly (2-oxazoline-co-ethyleneimine)-epichlorohydrin are disclosed in U.S. Pat. Appl. Pub. No. US 2016/0061995 A1 (herein incorporated by reference in its entirety).

An "epichlorohydrin-functionalized polyamine" or "epichlorohydrin-functionalized polyamidoamine" refers to a polymer obtained by reacting a polyamine or polyamidoamine with epichlorohydrin to convert all or a substantial percentage of the secondary amine groups of the polyamine or polyamidoamine into azetidinium groups.

The term "polyamidoamine-epichlorohydrin" refers to an epichlorohydrin-functionalized adipic acid-diethylenetriamine copolymer.

The term "thermally-crosslinkable" in reference to a polymeric material or a functional group means that the polymeric material or the functional group can undergo a crosslinking (or coupling) reaction with another material or functional group at a relatively-elevated temperature (from about 40° C. to about 140° C.), whereas the polymeric material or functional group cannot undergo the same crosslinking reaction (or coupling reaction) with another material or functional group at room temperature (i.e., from about 22° C. to about 28° C., preferably from about 24° C. to about 26° C., in particular at about 25° C.) to an extend detectable for a period of about one hour.

An "initiator" refers to a chemical that can initiate free radical crosslinking/polymerizing reaction.

A "spatial limitation of actinic radiation" refers to an act or process in which energy radiation in the form of rays is directed by, for example, a mask or screen or combinations thereof, to impinge, in a spatially restricted manner, onto an area having a well-defined peripheral boundary. A spatial limitation of UV radiation is obtained by using a mask or screen having a radiation (e.g., UV and/or visible light) permeable region, a radiation (e.g., UV and/or visible light) impermeable region surrounding the radiation-permeable region, and a projection contour which is the boundary between the radiation-impermeable and radiation-permeable regions, as schematically illustrated in the drawings of U.S. Pat. No. 6,800,225 (FIGS. 1-11), and U.S. Pat. No. 6,627,124 (FIGS. 1-9), U.S. Pat. No. 7,384,590 (FIGS. 1-6), and U.S. Pat. No. 7,387,759 (FIGS. 1-6), all of which are incorporated by reference in their entireties. The mask or screen allows to spatially projects a beam of radiation (e.g., UV radiation and/or visible radiation) having a cross-sectional profile defined by the projection contour of the mask or screen. The projected beam of radiation (e.g., UV radiation and/or visible radiation) limits radiation impinging on a lens formulation located in the path of the projected beam from the first molding surface to the second molding surface of a mold. The resultant contact lens comprises an anterior surface defined by the first molding surface, an opposite posterior surface defined by the second molding surface, and a lens edge defined by the sectional profile of the projected UV and/or visible beam (i.e., a spatial limitation of radiation). The radiation used for the crosslinking is radiation energy, especially UV radiation (and/or visible radiation), gamma radiation, electron radiation or thermal radiation, the radiation energy preferably being in the form of a substantially parallel beam in order on the one hand to achieve good restriction and on the other hand efficient use of the energy.

The term "modulus" or "elastic modulus" in reference to a contact lens or a material means the tensile modulus or Young's modulus which is a measure of the stiffness of a contact lens or a material. The modulus can be measured using a method in accordance with ANSI Z80.20 standard. A person skilled in the art knows well how to determine the elastic modulus of a silicone hydrogel material or a contact lens. For example, all commercial contact lenses have reported values of elastic modulus.

In general, the invention is directed to a method for producing soft contact lenses each of which comprises a polyvinylalcohol-based hydrogel lens body and a covalently attached lubricious coating and to such soft contact lenses. The invention is partly based on the discovery that a polyvinylalcohol-based hydrogel contact lens can be coated with a hydrophilic polymer having reactive groups each capable of reacting with one 1,3-diol unit to form a 6-membered ring, as illustrated in Scheme I, to chemically attach a layer (or coating) of the hydrophilic polymer, in a water-based coating process. The formed acetal rings are highly stable against hydrolytical or thermal decomposition reactions and thereby the layer (or coating) of the hydrophilic polymer is stably anchored onto the polyvinylalcohol-based contact lens for enhancing the surface lubricity of the polyvinylalcohol-based contact lens. That layer (or coating) of the hydrophilic polymer can also be used as an anchor layer (or coating) for covalently attaching one or more other hydrophilic polymers to form a hydrogel top layer (or coating). It is further discovered that the water-based coating process has no or minimal impact on the properties of the preformed non-silicone hydrogel contact lens so as to maintain all the beneficial attributes of the preformed non-silicone hydrogel contact lens, for example, such as, softness, elongation, eye-blink-induced lubricant release, etc.

Scheme I

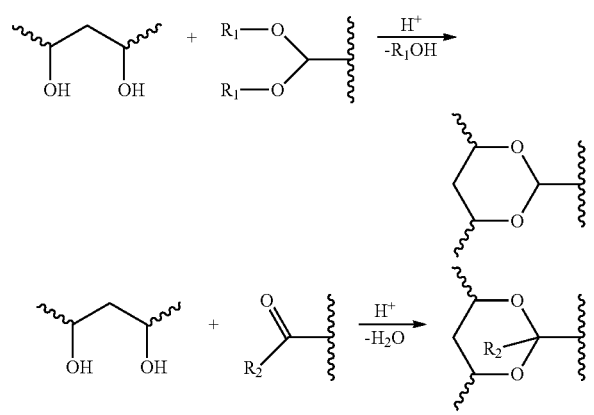

In one aspect, the invention provides a method for producing soft contact lenses, comprising the steps of: (1) obtaining a preformed polyvinylalcohol-based hydrogel contact lens, wherein the preformed polyvinylalcohol-based hydrogel contact lens is composed of a polymer comprising at least 50% by mole (preferably at least 60% by mole, more preferably at least 70% by mole, even more preferably at least 75% by mole) of repeating units of vinyl alcohol; (2) contacting the preformed polyvinylalcohol-based hydrogel contact lens with a first aqueous coating solution of a hydrophilic polymer having reactive groups of

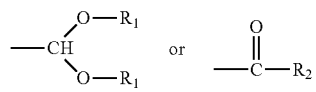

in which $R_1$ is methyl or ethyl (preferably methyl) and $R_2$ is hydrogen or a $C_1$-$C_4$ alkyl (preferably hydrogen), at a pH of about 4.0 or less (preferably about 3.5 or less, more preferably about 3.0 or less, even more preferably from about 0.5 to about 2.5) for a contacting time period to covalently attach a layer (or coating) of the hydrophilic polymer onto the preformed polyvinylalcohol-based hydrogel contact lens through 6-membered acetal rings.

Any suitable preformed polyvinylalcohol-based hydrogel contact lenses can be used in the invention, so long as they are composed of a polymer comprising at least 50% by mole (preferably at least 60% by mole, more preferably at least 70% by mole, even more preferably at least 75% by mole of repeating units of vinyl alcohol.

In accordance with the invention, a preformed hydrogel contact lens is a contact lens that has not been subjected to any surface modification posterior to the lens-forming process well known to a person skilled in the art. For example, preformed contact lenses can be produced in a conventional "spin-casting mold," as described for example in U.S. Pat. No. 3,408,429, or by the full cast-molding process in a static form, as described in U.S. Pat. Nos. 4,347,198; 5,508,317; 5,583,463; 5,789,464; and 5,849,810, or by lathe cutting of buttons as used in making customized contact lenses. In cast-molding, a lens formulation typically is dispensed into molds and cured (i.e., polymerized and/or crosslinked) in molds for making contact lenses.

For production of preformed hydrogel contact lenses, a hydrogel lens formulation typically is: either (1) a monomer mixture comprising (a) at least one hydrophilic vinylic monomer (e.g., hydroxyethyl methacrylate, glycerol methacrylate, N-vinylpyrrolidone, or combinations thereof) and (b) at least one component selected from the group consisting of a crosslinking agent, a hydrophobic vinylic monomer, a lubricating agent (or so-called internal wetting agents incorporated in a lens formulation), a free-radical initiator (photoinitiator or thermal initiator), a UV-absorbing agent, a visibility tinting agent (e.g., dyes, pigments, or mixtures thereof), antimicrobial agents (e.g., preferably silver nanoparticles), a bioactive agent, and combinations thereof; or (2) an aqueous solution comprising one or more water-soluble prepolymers and at least one component selected from the group consisting of hydrophilic vinylic monomer, a crosslinking agent, a hydrophobic vinylic monomer, a lubricating agent (or so-called internal wetting agents incorporated in a lens formulation), a free-radical initiator (photoinitiator or thermal initiator), a UV-absorbing agent, a visibility tinting agent (e.g., dyes, pigments, or mixtures thereof), antimicrobial agents (e.g., preferably silver nanoparticles), a bioactive agent, and combinations thereof. Resultant preformed hydrogel contact lenses then can be subjected to extraction with an extraction solvent to remove unpolymerized components from the resultant lenses and to hydration process, as known by a person skilled in the art. It is understood that a lubricating agent present in a hydrogel lens formulation can improve the lubricity of preformed hydrogel contact lenses compared to the lubricity of control preformed hydrogel contact lenses obtained from a control hydrogel lens formulation without the lubricating agent.

In a preferred embodiment, a preformed polyvinylalcohol-based hydrogel contact lens is preferably obtained by polymerizing a water-soluble, actinically-crosslinkable polyvinyl alcohol prepolymer, comprising:

repeating units of vinyl alcohol (i.e.,

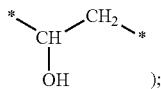

);

repeating crosslinking units of formula (I); and

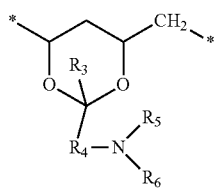

in which:
$R_3$ can be hydrogen or a $C_1$-$C_6$ alkyl group (preferably hydrogen);
$R_4$ is a $C_1$-$C_6$ alkylene divalent radical (preferably a $C_1$-$C_4$ alkylene divalent radical, more preferably methylene or butylene divalent radical, even more preferably methylene divalent radical);
$R_5$ is hydrogen or $C_1$-$C_6$ alkyl (preferably hydrogen or $C_1$-$C_4$ alkyl, more preferably hydrogen or methyl or ethyl, even more preferably hydrogen or methyl);
$R_6$ is an ethylenically unsaturated group of

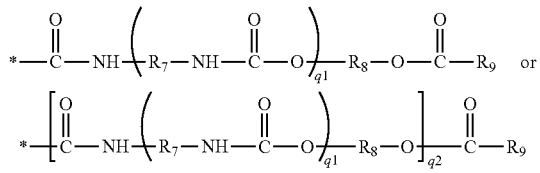

in which q1 and q2 independently of each another are zero or one, and $R_7$ and $R_8$ independently of one another are a $C_2$-$C_8$ alkylene divalent radical, $R_9$ is $C_2$-$C_8$ alkenyl.

In another preferred embodiment, wherein $R_4$ is methylene divalent radical, $R_5$ is hydrogen or $C_1$-$C_4$ alkyl, $R_3$ is hydrogen, and $R_6$ is a radical of $$*-\left[\begin{matrix}O\\\|\\C\end{matrix}-NH-\left(R_7-NH-\begin{matrix}O\\\|\\C\end{matrix}-O\right)_{q1}R_8-O\right]_{q2}\begin{matrix}O\\\|\\C\end{matrix}-R_9$$

in which q2 is zero, $R_9$ is vinyl (*—CH=$CH_2$) or 1-methylethenyl (*—C($CH_3$)=$CH_2$).

In another preferred embodiment, the polyvinylalcohol prepolymer has a weight average molecular weight of at least about 2,000 Daltons, and comprises from about 1% to about 25% by mole, preferably from about 2% to about 15% by mole of the repeating units of formula (I).

A water-soluble, actinically-crosslinkable polyvinylalcohol prepolymer can be prepared using techniques known in the art, e.g., those disclosed in U.S. Pat. Nos. 5,583,163 and 6,303,687 (herein incorporated by references in their entireties).

Preferably, the polyvinylalcohol prepolymers are purified in a manner known per se, for example by precipitation with organic solvents, such as acetone, filtration and washing, extraction in a suitable solvent, dialysis or ultrafiltration, ultrafiltration being especially preferred. By means of that purification process the prepolymers can be obtained in extremely pure form, for example in the form of concentrated aqueous solutions that are free, or at least substantially free, from reaction products, such as salts, and from starting materials, such as, for example, non-polymeric constituents.

The preferred purification process for the prepolymers used in the process according to the invention, ultrafiltration, can be carried out in a manner known per se. It is possible for the ultrafiltration to be carried out repeatedly, for example from two to ten times. Alternatively, the ultrafiltration can be carried out continuously until the selected degree of purity is attained. The selected degree of purity can in principle be as high as desired. A suitable measure for the degree of purity is, for example, the concentration of dissolved salts obtained as by-products, which can be determined simply in known manner.

It would be advantageous that the water-soluble actinically-crosslinkable polyvinylalcohol prepolymers are in a substantially pure form (e.g., purified by ultrafiltration to remove most reactants for forming the prepolymer). Therefore, after crosslinking by actinic radiation, a contact lens may require practically no more subsequent purification, such as in particular complicated extraction of unpolymerized constituents. Furthermore, crosslinking may take place in aqueous solution, so that a subsequent solvent exchange or the hydration step is not necessary.

Preferably, a preformed polyvinylalcohol-based hydrogel contact lens is obtained by: introducing an aqueous lens-forming composition including a water-soluble, actinically-crosslinkable polyvinyl alcohol prepolymer described above into a reusable mold and curing under a spatial limitation of actinic radiation the aqueous lens-forming composition.

Preferably, a reusable mold suitable for spatial limitation of radiation is used in the invention, the projected beam of radiation (e.g., radiation from the light source including the light in the region of 360 nm to 550 nm) limits radiation (e.g., UV radiation) impinging on the mixture of the lens-forming materials located in the path of the projected beam from the first molding surface to the second molding surface of the reusable mold. The resultant contact lens comprises an anterior surface defined by the first molding surface, an opposite posterior surface defined by the second molding surface, and a lens edge (with sharp edge and high quality) defined by the sectional profile of the projected radiation beam (i.e., a spatial limitation of radiation). Examples of reusable molds suitable for spatial limitation of radiation include without limitation those disclosed in U.S. Pat. Nos. 6,627,124, 6,800,225, 7,384,590, and 7,387,759, which are incorporated by reference in their entireties.

For example, a preferred reusable mold comprises a first mold half having a first molding surface and a second mold half having a second molding surface. The two mold halves of the preferred reusable mold are not touching each other, but there is a thin gap of annular design arranged between the two mold halves. The gap is connected to the mold cavity formed between the first and second molding surfaces, so that excess mixture can flow into the gap. It is understood that gaps with any design can be used in the invention.

In a preferred embodiment, at least one of the first and second molding surfaces is permeable to a crosslinking radiation. More preferably, one of the first and second molding surfaces is permeable to a crosslinking radiation while the other molding surface is poorly permeable to the crosslinking radiation.

The reusable mold preferably comprises a mask which is fixed, constructed or arranged in, at or on the mold half having the radiation-permeable molding surface. The mask is impermeable or at least of poor permeability compared with the permeability of the radiation-permeable molding surface. The mask extends inwardly right up to the mold cavity and surrounds the mold cavity so as to screen all areas behind the mask with the exception of the mold cavity.

The mask may preferably be a thin chromium layer, which can be produced according to processes as known, for example, in photo and UV lithography. Other metals or metal oxides may also be suitable mask materials. The mask can also be coated with a protective layer, for example of silicon dioxide if the material used for the mold or mold half is quartz.

Alternatively, the mask can be a masking collar made of a material comprising a UV/visible light-absorber and substantially blocks curing energy therethrough as described in U.S. Pat. No. 7,387,759 (incorporated by reference in its entirety). In this preferred embodiment, the mold half with the mask comprises a generally circular disc-shaped transmissive portion and a masking collar having an inner diameter adapted to fit in close engagement with the transmissive portion, wherein said transmissive portion is made from an optically clear material and allows passage of curing energy therethrough, and wherein the masking collar is made from a material comprising a light-blocker and substantially blocks passage of curing energy therethrough, wherein the masking collar generally resembles a washer or a doughnut, with a center hole for receiving the transmissive portion, wherein the transmissive portion is pressed into the center opening of the masking collar and the masking collar is mounted within a bushing sleeve.

Reusable molds can be made of quartz, glass, sapphire, CaF$_2$, a cyclic olefin copolymer (such as for example, Topas® COC grade 8007-S10 (clear amorphous copolymer of ethylene and norbornene) from Ticona GmbH of Frankfurt, Germany and Summit, N.J., Zeonex® and Zeonor® from Zeon Chemicals LP, Louisville, Ky.), polymethylmethacrylate (PMMA), polyoxymethylene from DuPont (Delrin), Ultern® (polyetherimide) from G.E. Plastics, PrimoSpire®, etc. Because of the reusability of the mold halves, a relatively high outlay can be expended at the time of their production in order to obtain molds of extremely high precision and reproducibility. Since the mold halves do not touch each other in the region of the lens to be produced, i.e. the cavity or actual molding surfaces, damage as a result of contact is ruled out. This ensures a high service life of the molds, which, in particular, also ensures high reproducibility of the contact lenses to be produced and high fidelity to the lens design.

In accordance with the invention, contacting of a preformed polyvinylalcohol-base hydrogel contact lens with a first aqueous coating solution of a hydrophilic polymer with reactive groups can occur by dipping it into the first aqueous coating solution or by spraying it with the first aqueous coating solution. One contacting process involves solely dipping the preformed polyvinylalcohol-base hydrogel contact lens in a bath of a first aqueous coating solution for a period of time or alternatively dipping the preformed polyvinylalcohol-base hydrogel contact lens sequentially in a series of bath of first aqueous coating solutions for a fixed shorter time period for each bath. Another contacting process involves solely spray a first aqueous coating solution. However, a number of alternatives involve various combinations of spraying- and dipping-steps may be designed by a person having ordinary skill in the art. Preferably, the step of contacting is performed by dipping the preformed polyvinylalcohol-base hydrogel contact lens in the first aqueous coating solution.

The first aqueous coating solution has a pH of about 4 or less, preferably about 3.5 or less, more preferably about 3.0 or less, even more preferably from about 0.5 to about 2.5.

The first aqueous coating solution has a temperature of preferably from about 35° C. to about 85° C., more preferably from about 40° C. to about 80° C., even more preferably from about 45° C. to about 70° C.

The contacting time period is preferably about 30 minutes or less, more preferably about 20 minutes or less, even more preferably about 10 minutes or less, most preferably about 5 minutes or less.

Any suitable hydrophilic polymers can be used in the invention so long they are water-soluble and comprise about 25% or less by mole (preferably about 20% or less by mole, more preferably about 15% or less by mole, even more preferably about 10% or less by mole) of repeating units of a vinylic monomer having a reactive group of

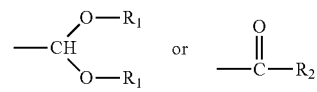

in which $R_1$ is methyl or ethyl (preferably methyl) and $R_2$ is hydrogen or a $C_1$-$C_4$ alkyl (preferably hydrogen). They can be linear or branched polymers. Such hydrophilic polymers can be prepared by copolymerizing one or more vinylic monomer having a reactive group of

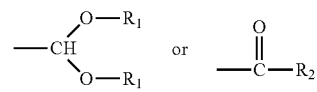

with one or more hydrophilic vinylic monomer in the presence of a vinylic crosslinking agent (i.e., for forming linear polymers) or in the absence of a vinylic crosslinking agent (i.e., for forming branched polymers), according to any polymerization techniques known to a person skilled in the art.

Examples of vinylic monomers having a reactive group of

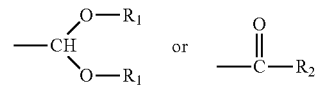

include without limitation acrolein, methacrolein, crotonaldehyde, acrolein dimethyl acetal, acrolein diethyl acetal, methacrolein dimethyl acetal, methacrolein diethyl acetal, methyl vinyl ketone, 3-methyl-3-buten-2-one, 3-penten-2-one, ethyl vinyl ketone, propyl vinyl ketone, isopropyl vinyl ketone, vinyl butyl ketone, tert-butyl vinyl ketone, iso-butyl vinyl ketone, methyl allyl ketone, and combinations thereof.

Any suitable hydrophilic vinylic monomers can be used. Examples of suitable hydrophilic vinylic monomers include without limitation carboxyl-containing vinylic monomers, primary amine-containing vinylic monomers, secondary amine-containing vinylic monomer, non-reactive hydrophilic vinylic monomers, phosphorylcholine-containing vinylic monomers, and combinations thereof.

Examples of preferred carboxyl-containing vinylic monomers include without limitation acrylic acid, methacrylic ethylacrylic acid, propylacrylic acid, butylacrylic acid, N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carobxy-4-phenyl butadiene-1,3, itaconic acid, citraconic acid, mesaconic acid, glutaconic acid, aconitic acid, maleic acid, fumaric acid, tricarboxy ethylene, and combinations thereof.

Examples of preferred primary and secondary amino-containing vinylic monomers include without limitation amino-$C_2$-$C_6$ alkyl (meth)acrylate, $C_1$-$C_6$ alkylamino-$C_2$-$C_6$ alkyl (meth)acrylate, allylamine, vinylamine, amino-$C_2$-$C_6$ alkyl (meth)acrylamide, $C_1$-$C_6$ alkylamino-$C_2$-$C_6$ alkyl (meth)acrylamide, and combinations thereof.

In accordance with the invention, a non-reactive vinylic monomer is a vinylic monomer free of any carboxyl group, primary amine group, secondary amine group, epoxide group, isocyanate group, azlactone group, or aziridine group. Examples of preferred non-reactive hydrophilic vinylic monomers include without limitation (meth)acrylamide, N,N-dimethyl (meth)acrylamide, N-vinylpyrrolidone (NVP), N-vinyl formamide, N-vinyl acetamide, N-vinyl isopropylamide, N-vinyl-N-methyl acetamide, N,N-dimethylaminoethyl (meth)acrylate, N,N-dimethylaminopropyl (meth)acrylamide, glycerol (meth)acrylate, 3-(meth)acryloylamino-1-propanol, N-hydroxyethyl (meth)acrylamide, N-hydroxypropyl (meth)acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, hydroxypropyl (meth)acrylate, $C_1$-$C_4$-alkoxy polyethylene glycol (meth)acrylate having a weight average molecular weight of up to 1500 Daltons, allyl alcohol, vinyl alcohol, and combinations thereof.

Examples of preferred phosphorylcholine-containing vinylic monomers include without limitation (meth)acryloyloxyethyl phosphorylcholine (aka, MPC, or 2-((meth)acryloyloxy)ethyl-2'-(trimethylammonio)ethylphosphate), (meth)acryloyloxypropyl phosphorylcholine (aka, 3-((meth)acryloyloxy)propyl-2'-(trimethylammonio)ethylphosphate), 4-((meth)acryloyloxy)butyl-2'-(trimethylammonio)ethylphosphate, 2-[(meth)acryloylamino]ethyl-2'-(trimethylammonio)ethylphosphate, 3-[(meth)acryloylamino]propyl-2'-(trimethylammonio)ethylphosphate, 4-[(meth)acryloylamino]butyl-2'-(trimethylammonio)ethylphosphate, 5-((meth)acryloyloxy)pentyl-2'-(trimethylammonio)ethyl phosphate, 6-((meth)acryloyloxy)hexyl-2'-(trimethylammonio)-ethylphosphate, 2-((meth)acryloyloxy)ethyl-2'-(triethylammonio)ethylphosphate, 2-((meth)acryloyloxy)ethyl-2'-(tripropylammonio)ethylphosphate, 2-((meth)acryloyloxy)ethyl-2'-(tributylammonio)ethyl phosphate, 2-((meth)acryloyloxy)propy-2'-(trimethylammonio)-ethylphosphate, 2-((meth)acryloyloxy)butyl-2'-(trimethylammonio)ethylphosphate, 2-((meth)acryloyloxy)pentyl-2'-(trimethylammonio)ethylphosphate, 2-((meth)acryloyloxy)hexyl-2'-(trimethylammonio)ethyl phosphate, 2-(vinyloxy)ethyl-2'-(trimethylammonio)ethylphosphate, 2-(allyoxy)ethyl-2'-(trimethylammonio)ethylphosphate, 2-(vinyloxycarbonyl)ethyl-2"-(trimethylammonio)ethyl phosphate, 2-(allyloxycarbonyl)ethyl-2'-(trimethylammonio)-ethylphosphate, 2-(vinylcarbonylamino)ethyl-2'-(trimethylammonio)ethylphosphate, 2-(allyloxycarbonylamino)ethyl-2'-(trimethylammonio)ethyl phosphate, 2-(butenoyloxy)ethyl-2'-(trimethylammonio)ethylphosphate, and combinations thereof. Phosphorylcholine-containing vinylic monomers can be prepared according to procedures described in U.S. Pat. Nos. 5,461,433 and 5,741,923 (herein incorporated by references in their entireties).

In a preferred embodiment, the hydrophilic polymer comprises repeating units of one or more vinylic monomers selected from the group consisting of acryamide, N,N-dimethylacrylamide, N-vinylpyrrolidone, (meth)acryloyloxyethyl phosphorylcholine, N-vinyl-N-methyl acetamide, glycerol (meth)acrylate, hydroxyethyl (meth)acrylate, N-hydroxyethyl (meth)acrylamide, $C_1$-$C_4$-alkoxy polyethylene glycol (meth)acrylate having a weight average molecular weight of up to 400 Daltons, vinyl alcohol, and combination thereof.

In another preferred embodiment, the hydrophilic polymer comprises repeating units of one or more vinylic monomers selected from the group consisting of a carboxyl-containing vinylic monomer, a primary amine-containing vinylic monomer, a secondary amine-containing vinylic monomer, and combinations thereof. In this embodiment, the method of the invention can further comprise a step of heating the polyvinylalcohol-based hydrogel contact lens having the layer (or coating) of the hydrophilic polymer thereon in a second aqueous coating solution comprising a water-soluble thermally-crosslinkable polymeric material having azetidinium groups to form a hydrogel layer (or coating) on top of the layer (or coating) of the hydrophilic polymer.

In accordance with the invention, a water-soluble and thermally-crosslinkable hydrophilic polymeric material must comprise azetidinium groups and is a partial reaction product of at least one azetidinium-containing polymer with at least one hydrophilicity-enhancing agent (i.e., a wetting agent) having at least one carboxyl, primary amine, secondary amine, or thiol group, according to the crosslinking reactions shown in Scheme II Scheme II

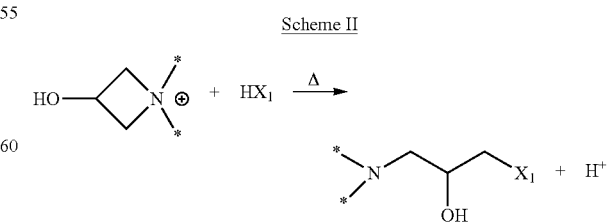

in which $X_1$ is —S—*, —OC(=O)—*, or —NR'—* in which R' is hydrogen or a $C_1$-$C_{20}$ unsubstituted or substituted alkyl group, and * represents an organic radical.

Any suitable azetidinium-containing polymers can be used in the invention. Examples of azetidinium-containing polymers includes without limitation epichlorohydrin-functionalized polyamines, homopolymers of an azetidinium-containing vinylic monomer, copolymers of an azetidinium-containing vinylic monomer with one or more vinylic monomers.

Preferably, an azetidinium-containing polymer is an epichlorohydrin-functionalized polyamine. An epichlorohydrin-functionalized polyamine can be obtained by reacting epichlorohydrin with a polyamine polymer or a polymer containing secondary amino groups. For example, a poly(alkylene imines) or a poly(amidoamine) which is a polycondensate derived from a polyamine and a dicarboxylic acid (e.g., adipic acid-diethylenetriamine copolymers) can react with epichlorohydrin to form an epichlorohydrin-functionalized polymer; a homopolymer or copolymer of mono-alkylaminoalkyl (meth)acrylate or mono-alkylaminoalkyl (meth)acrylamide can also react with epichlorohydrin to form an epichlorohydrin-functionalized polyamine; a poly(2-oxazoline-co-ethyleneimine) copolymer can react with epichlorohydrin to form an epichlorohydrin-functionalized polyamine (i.e., a poly(2-oxazoline-co-ethyleneimine)-epichlorohydrin). The reaction conditions for epichlorohydrin-functionalization of a polyamine or polyamidoamine polymer are taught in EP1465931 (herein incorporated by reference in its entirety). A preferred epichlorohydrin-functionalized polyamine is polyamidoamine-epichlorohydrin (PAE) or a poly(2-oxazoline-co-ethyleneimine)-epichlorohydrin.

Polyamidoamine-epichlorohydrin is commercially available, such as, for example, Kymene® or Polycup® resins (epichlorohydrin-functionalized adipic acid-diethylenetriamine copolymers) from Hercules.

Poly(2-oxazoline-co-ethyleneimine)-epichlorohydrin can be prepared according to procedures described in U.S. Pat. Appl. Pub. No. US 2016/0061995 A1 (herein incorporated by reference in its entirety).

Homopolymers and copolymers of an azetidinium-containing vinylic monomer can be obtained according to the procedures described in U.S. Pat. Appl. Pub. No. 2013/0337160A1 (herein incorporated by reference in its entirety).

Any suitable hydrophilicity-enhancing agents can be used in the invention so long as they are ophthalmically compatible and contain at least one amino group, at least one carboxyl group, and/or at least one thiol group.

A preferred class of hydrophilicity-enhancing agents include without limitation: primary amino-, secondary amino-, carboxyl- or thiol-containing monosaccharides (e.g., 3-amino-1,2-propanediol, 1-thiolglycerol, 5-keto-D-gluconic acid, galactosamine, glucosamine, galacturonic acid, gluconic acid, glucosaminic acid, mannosamine, saccharic acid 1,4-lactone, saccharide acid, Ketodeoxynonulosonic acid, N-methyl-D-glucamine, 1-amino-1-deoxy-β-D-galactose, 1-amino-1-deoxysorbitol, 1-methylamino-1-deoxysorbitol, N-aminoethyl gluconamide); primary amino-, secondary amino-, carboxyl- or thiol-containing disaccharides (e.g., chondroitin disaccharide sodium salt, di(β-D-xylopyranosyl)amine, digalacturonic acid, heparin disaccharide, hyaluronic acid disaccharide, Lactobionic acid); and primary amino-, secondary amino-, carboxyl- or thiol-containing oligosaccharides (e.g., carboxymethyl-β-cyclodextrin sodium salt, trigalacturonic acid); and combinations thereof.

Another preferred class of hydrophilicity-enhancing agents is hydrophilic polymers having one or more (primary or secondary) amino, carboxyl and/or thiol groups. More preferably, the content of the amino (—NHR' with R' as defined above), carboxyl (—COOH) and/or thiol (—SH) groups in a hydrophilic polymer as a hydrophilicity-enhancing agent is less than about 40%, preferably less than about 30%, more preferably less than about 20%, even more preferably less than about 10%, by weight based on the total weight of the hydrophilic polymer.

One preferred class of hydrophilicity-enhancing agents are (primary or secondary) amino- or carboxyl-containing polysaccharides, for example, such as, carboxymethylcellulose (having a carboxyl content of about 40% or less, which is estimated based on the composition of repeating units, —[$C_6H_{10-m}O_5(CH_2CO_2H)_m$]— in which m is 1 to 3), carboxyethylcellulose (having a carboxyl content of about 36% or less, which is estimated based on the composition of repeating units, —[$C_6H_{10-m}O_5(C_2H_4CO_2H)_m$]— in which m is 1 to 3) carboxypropylcellulose (having a carboxyl content of about 32% or less, which is estimated based on the composition of repeating units, —[$C_6H_{10-m}O_5(C_3H_6CO_2H)_m$]—, in which m is 1 to 3), hyaluronic acid (having a carboxyl content of about 11%, which is estimated based on the composition of repeating units, —($C_{13}H_{20}O_9NCO_2H$)—), chondroitin sulfate (having a carboxyl content of about 9.8%, which is estimated based on the composition of repeating units, —($C_{12}H_{18}O_{13}NS CO_2H$)—), or combinations thereof.

Another preferred class of hydrophilicity-enhancing agents include without limitation: poly(ethylene glycol) (PEG) with mono-amino (primary or secondary amino), carboxyl or thiol group (e.g., PEG-$NH_2$, PEG-SH, PEG-COOH); $H_2N$-PEG-$NH_2$; HOOC-PEG-COOH; HS-PEG-SH; $H_2N$-PEG-COOH; HOOC-PEG-SH; $H_2N$-PEG-SH; multi-arm PEG with one or more amino (primary or secondary), carboxyl or thiol groups; PEG dendrimers with one or more amino (primary or secondary), carboxyl or thiol groups; a diamino-(primary or secondary) or dicarboxyl-terminated homo- or co-polymer of a non-reactive hydrophilic vinylic monomer; a monoamino- (primary or secondary) or monocarboxyl-terminated homo- or co-polymer of a non-reactive hydrophilic vinylic monomer (any one of those described above) or a phosphorylcholine-containing vinylic monomer (any one of those described above); a copolymer which is a polymerization product of a composition comprising (1) about 60% by weight or less, preferably from about 0.1% to about 30%, more preferably from about 0.5% to about 20%, even more preferably from about 1% to about 15%, by weight of one or more reactive vinylic monomers and (2) at least one non-reactive hydrophilic vinylic monomer; and combinations thereof.

In accordance with the invention, reactive vinylic monomers can be carboxyl-containing vinylic monomers (any those preferred examples described above), primary amino-containing vinylic monomers (any those preferred examples described above), or secondary amino-containing vinylic monomers (any those preferred examples described above).

More preferably, a hydrophilicity-enhancing agent is PEG-N $H_2$; PEG-SH; PEG-COOH; $H_2N$-PEG-$NH_2$; HOOC-PEG-COOH; HS-PEG-SH; $H_2N$-PEG-COOH; HOOC-PEG-SH; $H_2N$-PEG-SH; multi-arm PEG with one or more amino, carboxyl or thiol groups; PEG dendrimers with one or more amino, carboxyl or thiol groups; a mono-amino-, monocarboxyl-, diamino- or dicarboxyl-terminated homo- or copolymer of a non-reactive hydrophilic vinylic monomer selected from the group consisting of (meth)acryamide, N-vinyl pyrrolidone (NVP), N-vinyl-N-methyl acetamide, glycerol (meth)acrylate, hydroxyethyl (meth)

acrylate, N-hydroxyethyl (meth)acrylamide, N-hydroxypropyl (meth)acrylamide, $C_1$-$C_4$-alkoxy polyethylene glycol (meth)acrylate having a weight average molecular weight of up to 400 Daltons, vinyl alcohol, N-methyl-3-methylene-2-pyrrolidone, 1-methyl-5-methylene-2-pyrrolidone, 5-methyl-3-methylene-2-pyrrolidone, N,N-dimethylaminoethyl (meth)acrylate, N,N-dimethylaminopropyl (metha)crylamide, (meth)acryloyloxyethyl phosphorylcholine, and combinations thereof; a copolymer which is a polymerization product of a composition comprising (1) from about 0.1% to about 30%, preferably from about 0.5% to about 20%, more preferably from about 1% to about 15%, by weight of acrylic acid, $C_1$-$C_3$ alkylacrylic acid, allylamine and/or amino-$C_2$-$C_4$ alkyl (meth)acrylate, and (2) at least one non-reactive hydrophilic vinylic monomer selected from the group consisting of acryamide, N,N-dimethylacrylamide, N-vinylpyrrolidone, (meth)acryloyloxyethyl phosphorylcholine, N-vinyl-N-methyl acetamide, glycerol (meth)acrylate, hydroxyethyl (meth)acrylate, N-hydroxyethyl (meth)acrylamide, $C_1$-$C_4$-alkoxy polyethylene glycol (meth)acrylate having a weight average molecular weight of up to 400 Daltons, vinyl alcohol, and combination thereof.

Most preferably, a hydrophilicity-enhancing agent is PEG-N $H_2$; PEG-SH; PEG-COOH; monoamino-, monocarboxyl-, diamino- or dicarboxyl-terminated polyvinylpyrrolidone; monoamino-, monocarboxyl-, diamino- or dicarboxyl-terminated polyacrylamide; monoamino-, monocarboxyl-, diamino- or dicarboxyl-terminated poly(DMA); monoamino- or monocarboxyl-, diamino- or dicarboxyl-terminated poly(DMA-co-NVP); monoamino-, monocarboxyl-, diamino- or dicarboxyl-terminated poly(NVP-co-N, N-dimethylaminoethyl (meth)acrylate)); monoamino-, monocarboxyl-, diamino- or dicarboxyl-terminated poly(vinylalcohol); monoamino-, monocarboxyl-, diamino- or dicarboxyl-terminated poly[(meth)acryloyloxyethyl phosphrylcholine] homopolymer or copolymer; monoamino-, monocarboxyl-, diamino- or dicarboxyl-terminated poly(NVP-co-vinyl alcohol); monoamino-, monocarboxyl-, diamino- or dicarboxyl-terminated poly(N,N-dimethylacrylamide-co-vinyl alcohol); poly[(meth)acrylic acid-co-acrylamide] with from about 0.1% to about 30%, preferably from about 0.5% to about 20%, more preferably from about 1% to about 15%, by weight of (meth)acrylic acid; poly[(meth)acrylic acid-co-NVP) with from about 0.1% to about 30%, preferably from about 0.5% to about 20%, more preferably from about 1% to about 15%, by weight of (meth)acrylic acid; a copolymer which is a polymerization product of a composition comprising (1) (meth)acryloyloxyethyl phosphorylcholine and (2) from about 0.1% to about 30%, preferably from about 0.5% to about 20%, more preferably from about 1% to about 15%, by weight of acrylic acid, $C_1$-$C_3$ alkylacrylic acid, allylamine and/or amino-$C_2$-$C_4$alkyl (meth)acrylate; and combination thereof.

PEGs with functional groups and multi-arm PEGs with functional groups can be obtained from various commercial suppliers, e.g., Polyscience, and Shearwater Polymers, inc., etc.

Monoamino-, monocarboxyl-, diamino- or dicarboxyl-terminated homo- or copolymers of one or more non-reactive hydrophilic vinylic monomers or of a phosphorylcholine-containing vinylic monomer can be prepared according to procedures described in U.S. Pat. No. 6,218,508, herein incorporated by reference in its entirety. For example, to prepare a diamino- or dicarboxyl-terminated homo- or co-polymer of a non-reactive hydrophilic vinylic monomer, the non-reactive vinylic monomer, a chain transfer agent with an amino or carboxyl group (e.g., 2-aminoethanethiol, 2-mercaptopropinic acid, thioglycolic acid, thiolactic acid, or other hydroxymercaptanes, aminomercaptans, or carboxyl-containing mercaptanes) and optionaly other vinylic monomer are copolymerized (thermally or actinically) with a reactive vinylic monomer (having an amino or carboxyl group), in the presence of an free-radical initiator. Generally, the molar ratio of chain transfer agent to that of all of vinylic monomers other than the reactive vinylic monomer is from about 1:5 to about 1:100, whereas the molar ratio of chain transfer agent to the reactive vinylic monomer is 1:1. In such preparation, the chain transfer agent with amino or carboxyl group is used to control the molecular weight of the resultant hydrophilic polymer and forms a terminal end of the resultant hydrophilic polymer so as to provide the resultant hydrophilic polymer with one terminal amino or carboxyl group, while the reactive vinylic monomer provides the other terminal carboxyl or amino group to the resultant hydrophilic polymer. Similarly, to prepare a monoamino- or monocarboxyl-terminated homo- or co-polymer of a non-reactive hydrophilic vinylic monomer, the non-reactive vinylic monomer, a chain transfer agent with an amino or carboxyl group (e.g., 2-aminoethanethiol, 2-mercaptopropinic acid, thioglycolic acid, thiolactic acid, or other hydroxymercaptanes, aminomercaptans, or carboxyl-containing mercaptanes) and optionally other vinylic monomers are copolymerized (thermally or actinically) in the absence of any reactive vinylic monomer.

Copolymers comprising a non-reactive hydrophilic vinylic monomer and a reactive vinylic monomer (e.g., a carboxyl-containing vinylic monomer, a primary amino group-containing vinylic monomer or a secondary amino group-containing vinylic monomer) can be prepared according to any well-known radical polymerization methods or obtained from commercial suppliers. Copolymers containing methacryloyloxyethyl phosphorylcholine and carboxyl-containing vinylic monomer (or amino-containing vinylic monomer) can be obtained from NOF Corporation (e.g., LIPIDURE®-A and -AF).

The weight average molecular weight $M_w$ of the hydrophilic polymer having at least one amino, carboxyl or thiol group (as a hydrophilicity-enhancing agent) is preferably from about 500 to about 5,000,000, more preferably from about 1,000 to about 2,000,000, even more preferably from about 5,000 to about 1,000,000 Daltons.

Water-soluble and thermally-crosslinkable hydrophilic polymeric materials can be prepared according to the processes disclosed in U.S. Pat. Appli. Pub. Nos. US 2016/0061995 A1 and US2013/0337160 A1 (herein incorporated by reference in their entireties) and in U.S. Pat. No. 8,529,057 (herein incorporated by reference in its entirety).

In a preferred embodiment, a water-soluble thermally-crosslinkable polymeric material can be obtained by heating an aqueous reactive solution, which comprises at least one azetidinium-containing polymer and at least one hydrophilicity-enhancing agent (i.e., a wetting agent) having at least one reactive functional group selected from the group consisting of amino group, carboxyl group, thiol group, and a combination thereof, to a temperature of from about 35° C. to about 85° C. and maintaining the temperature for a period of time sufficient (about 6 hours or less, preferably about 5 hours, more preferably from about 2 hour to about 4 hours). The aqueous reactive solution preferably comprises from about 70 mM to about 170 mM (preferably about 90 mM to about 150 mM, more preferably from about 100 mM to about 130 mM) of one or more ionic compounds and a pH of at least 7.0 (preferably at least 7.5 (preferably at least 8.0, more preferably at least 8.5, even more preferably at least 9.0). It should be understood that the reaction time should be long enough to covalently attach the hydrophilicity-enhancing agent onto the polymer chain of the azetidinium-containing polymer, but should be short enough not to consume all the azetidinium groups of the azetidinium-containing polymer and not to form a gel (i.e., not water-soluble) due to the too many crosslinkages formed between the azetidinium-containing polymer and the hydrophilicity-enhancing agent. A resultant polymeric material is a lightly-crosslinked polymeric material which has a highly-branched structure and still comprises thermally-crosslinkable azetidinium groups.

A person skilled in the art understands well how to adjust the pH of the reactive mixture, e.g., by adding a base (e.g., NaOH, KOH, $NH_4OH$, or mixture thereof) or an acid (e.g., HCl, $H_2SO_4$, $H_3PO_4$, citric acid, acetic acid, boric acid, or mixture thereof).

In accordance with the invention, any ionic compounds can be used in the reactive mixture. Preferably, ionic compounds are those used as ionic tonicity-adjusting agents and ionic buffering agents used in an ophthalmic solutions. Examples of preferred ionic tonicity-adjusting agents includes without limitation sodium chloride, potassium chloride, and combinations thereof. Examples of preferred ionic buffering agents includes various salts of phosphoric acid (e.g. $NaH_2PO_4$, $Na_2HPO_4$, $Na_3PO_4$, $KH_2PO_4$, $K_2HPO_4$, $K_3PO_4$, or mixtures thereof), various salts of boric acid (e.g., sodium borate, potassium borate, or mixture thereof), various salts of citric acid (e.g., monosodium citrate, disodium citrate, trisodium citrate, monopotassium citrate, dipotassium citrate, tripotassium citrate, or mixtures thereof), various salts of carbonic acid (e.g., $Na_2CO_3$, $NaHCO_3$, $K_2CO_3$, $KHCO_3$, or mixture thereof).

The aqueous reactive solution for preparing a water-soluble thermally-crosslinkable polymeric material can be prepared by dissolving a desired amount of an azetidinium-containing polymer, a desired amount of a hydrophilicity-enhancing agent with at least one reactive functional group, and desired amounts of other components (e.g., ionic buffering agents, ionic tonicity-adjusting agents, etc.) in water (or a mixture of water and a minority amount of a water-soluble organic solvent) to form an aqueous solution and then adjusting the pH of the aqueous solution if necessary.

In accordance with the invention, the concentration ratio of a hydrophilicity-enhancing agent relative to an azetidinium-containing polymer in the aqueous reactive solution must be selected not to render a resultant water-soluble thermally-crosslinkable polymeric material water-insoluble (i.e., a solubility of less than 0.005 g per 100 ml of water at room temperature) and not to consume more than about 99%, preferably about 98%, more preferably about 97%, even more preferably about 96% of the azetidinium groups of the azetidinium-containing polymer.

In a preferred embodiment, the aqueous reactive solution comprises from 0.01% to about 10% by weight (preferably from 0.05% to about 5% by weight, more preferably from 0.08% to about 1% by weight, even more preferably from 0.1% to about 0.4% by weight) of an azetidinium-containing polymer and from about 0.01% to about 10% by weight (preferably from 0.02% to about 5% by weight, more preferably from 0.05% to about 2% by weight, even more preferably from 0.08% to about 1.0% by weight) of a hydrophilicity-enhancing agent having at least one reactive function group (carboxyl, primary amino, secondary amino group), the concentration ratio of the azetidinium-containing polymer to the hydrophilicity-enhancing agent is from about 1000:1 to 1:1000 (preferably from about 500:1 to about 1:500, more preferably from about 250:1 to about 1:250, even more preferably from about 100:1 to about 1:100).

In a preferred embodiment, the water-soluble thermally-crosslinkable polymeric material comprises (i) from about 20% to about 95% by weight of first polymer chains derived from a polyamidoamine-epichlorohydrin or a poly(2-oxazoline-co-ethyleneimine)-epichlorohydrin, (ii) from about 5% to about 80% by weight of hydrophilic moieties or second polymer chains derived from at least one hydrophilicity-enhancing agent having at least one reactive functional group selected from the group consisting of amino group, carboxyl group, thiol group, and combination thereof (preferably carboxyl groups), wherein the hydrophilic moieties or second polymer chains are covalently attached to the first polymer chains through one or more covalent linkages each formed between one azetitdinium group of the polyamidoamine-epichlorohydrin or the poly(2-oxazoline-co-ethyleneimine)-epichlorohydrin and one amino, carboxyl or thiol group of the hydrophilicity-enhancing agent, and (iii) azetidinium groups which are parts of the first polymer chains or pendant or terminal groups covalently attached to the first polymer chains. The composition of a chemically-modified poly(2-oxazoline-co-ethyleneimine)-epichlorohydrin or a chemically-modified polyamidoamine-epichlorohydrin is determined by the composition (based on the total weight of the reactants) of a reactant mixture used for such a polymer according to the crosslinking reactions shown in Scheme I above. For example, if a reactant mixture comprises about 75% by weight of a polyamidoamine-epichlorohydrin and about 25% by weight of at least one hydrophilicity-enhancing agent based on the total weight of the reactants, then the resultant chemically-modified polyamidoamine-epichlorohydrin comprises about 75% by weight of first polymer chains derived from the polyamioamine-epichlorohydrin and about 25% by weight of hydrophilic moieties or second polymer chains derived from said at least one hydrophilicity-enhancing agent.

Preferably, the step of heating is performed by autoclaving the polyvinylalcohol-based hydrogel contact lens with the layer (or coating) of the hydrophilic polymer thereon in the second aqueous coating solution which is a packaging solution (i.e., a buffered aqueous solution with a pH of from 6.7 to 7.6) in a sealed lens package at a temperature of from about 115° C. to about 125° C. for approximately 20-90 minutes. It is believed that during autoclave those azetidinium groups which do not participate in crosslinking reaction may be hydrolyzed into 2,3-dihydroxypropyl ($HO-CH_2-CH(OH)-CH_2-$) groups and that the azetidinium-containing polymeric material present in the lens packaging solution, if applicable, can be converted to a non-reactive polymeric wetting agent capable of improving a lens's insert comfort. Consequently, the second aqueous coating solution is ophthalmically safe after autoclave.

Lens packages (or containers) are well known to a person skilled in the art for autoclaving and storing a soft contact lens. Any lens packages can be used in the invention. Preferably, a lens package is a blister package which comprises a base and a cover, wherein the cover is detachably sealed to the base, wherein the base includes a cavity for receiving a sterile packaging solution and the contact lens.

Lenses are packaged in individual packages, sealed, and sterilized (e.g., by autoclave at about 120° C. or higher for at least 30 minutes under pressure) prior to dispensing to users. A person skilled in the art will understand well how to seal and sterilize lens packages.

In accordance with the invention, a packaging solution contains at least one buffering agent and one or more other ingredients known to a person skilled in the art. Examples of other ingredients include without limitation, tonicity agents, surfactants, antibacterial agents, preservatives, and lubricants (e.g., cellulose derivatives, polyvinyl alcohol, polyvinyl pyrrolidone).

The packaging solution contains a buffering agent in an amount sufficient to maintain a pH of the packaging solution in the desired range, for example, preferably in a physiologically acceptable range of about 6.5 to about 7.5. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (2-amino-2-hydroxymethyl-1,3-propanediol), Bis-Tris (Bis-(2-hydroxyethyl)-imino-tris-(hydroxymethyl)-methane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N'-bis(2-ethanesulfonic acid), TES (N-[Tris(hydroxymethyl)methyl]-2-aminoethanesulfonic acid), salts thereof, phosphate buffers, e.g. $Na_2HPO_4$, $NaH_2PO_4$, and $KH_2PO_4$ or mixtures thereof. Preferably, the buffering agents are phosphate buffers, borate buffers, or combinations thereof. The amount of each buffer agent in a packaging solution is preferably from 0.001% to 2%, preferably from 0.01% to 1%; most preferably from about 0.05% to about 0.30% by weight.

The packaging solution has a tonicity of from about 200 to about 450 milliosmol (mOsm), preferably from about 250 to about 350 mOsm. The tonicity of a packaging solution can be adjusted by adding organic or inorganic substances which affect the tonicity. Suitable occularly acceptable tonicity agents include, but are not limited to sodium chloride, potassium chloride, glycerol, propylene glycol, polyols, mannitols, sorbitol, xylitol and mixtures thereof.

A packaging solution of the invention has a viscosity of from about 1 centipoise to about 5 centipoises, at 25° C.

In a preferred embodiment, the packaging solution comprises preferably from about 0.01% to about 2%, more preferably from about 0.05% to about 1.5%, even more preferably from about 0.1% to about 1%, most preferably from about 0.2% to about 0.5%, by weight of a water-soluble thermally-crosslinkable hydrophilic polymeric material having azetidinium groups.

In another aspect, the invention provides a soft contact lens which comprises a polyvinylalcohol-based hydrogel lens body; and a coating thereon, wherein the polyvinylalcohol-based hydrogel lens body is composed of a polymer comprising at least 50% by mole of repeating units of vinyl alcohol, wherein the coating comprises a layer of a hydrophilic polymer, wherein the hydrophilic polymer is a linear or branched polymer comprising about 20% or less by mole of repeating units of a vinylic monomer having a reactive group of

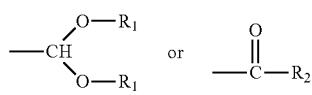

in which $R_1$ is methyl or ethyl and $R_2$ is hydrogen or a $C_1$-$C_4$ alkyl, wherein the layer of the hydrophilic polymer is covalently attached onto the polyvinylalcohol-based hydrogel lens body through 6-membered acetal rings, wherein the soft contact lens has a surface lubricity better than the lubricity of the polyvinylalcohol-based hydrogel lens body.

A polyvinylalcohol-based hydrogel lens body has a 3-dimensional shape of a contact lens. In accordance with the invention, a preformed polyvinylalcohol-based hydrogel contact lens becomes a polyvinylalcohol-based hydrogel lens body after being subjected to a surface treatment (here a coating process described above).

In a preferred embodiment, the coating further comprises a hydrogel layer which is covalently attached onto the layer of the hydrophilic polymer through linkages of

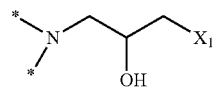

in which $X_1$ is

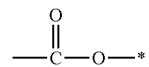

or —NR'—* in which R' is hydrogen or a $C_1$-$C_2$ alkyl group, and * represents an organic radical.

In accordance with the invention, the soft contact lens has a water content of preferably from about 15% to about 80%, more preferably from about 30% to about 70% by weight (at room temperature, about 22° C. to 28° C.), an elastic modulus of from about 0.2 MPa to about 1.5 MPa (preferably from about 0.3 MPa to about 1.3 MPa, more preferably from about 0.4 MPa to about 1.1 MPa, even more preferably from about 0.5 MPa to about 1.0 MPa, when fully hydrated.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A method for producing soft contact lenses, comprising the steps of:
(1) obtaining a preformed polyvinylalcohol-based hydrogel contact lens, wherein the preformed polyvinylalcohol-based hydrogel contact lens is composed of a polymer comprising at least 50% by mole of repeating units of vinyl alcohol;
(2) contacting the preformed polyvinylalcohol-based hydrogel contact lens with a first aqueous coating solution of a hydrophilic polymer having reactive groups of

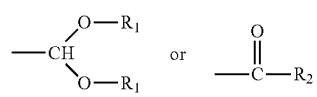

in which $R_1$ is methyl or ethyl and $R_2$ is hydrogen or a $C_1$-$C_4$ alkyl, at a pH of about 4.0 or less for a contacting time to covalently attach a layer (or coating) of the hydrophilic polymer onto the preformed polyvinylalcohol-based hydrogel contact lens through 6-membered acetal rings.

2. The method of invention 1, wherein the preformed polyvinylalcohol-based hydrogel contact lens is composed of a polymer comprising at least 60% by mole of repeating units of vinyl alcohol.

3. The method of invention 1, wherein the preformed polyvinylalcohol-based hydrogel contact lens is composed of a polymer comprising at least 70% by mole of repeating units of vinyl alcohol.

4. The method of invention 1, wherein the preformed polyvinylalcohol-based hydrogel contact lens is composed of a polymer comprising at least 75% by mole of repeating units of vinyl alcohol.

5. The method of any one of inventions 1 to 4, wherein $R_1$ is methyl and $R_2$ is hydrogen.

6. The method of any one of inventions 1 to 5, wherein the pH is about 3.5 or less.

7. The method of any one of inventions 1 to 5, wherein the pH is about 3.0 or less.

8. The method of any one of inventions 1 to 5, wherein the pH is from about 0.5 to about 2.5.

9. The method of any one of inventions 1 to 8, wherein the first aqueous coating solution has a temperature of from about 35° C. to about 85° C.

10. The method of any one of inventions 1 to 8, wherein the first aqueous coating solution has a temperature of from about 40° C. to about 80° C.

11. The method of any one of inventions 1 to 8, wherein the first aqueous coating solution has a temperature of from about 45° C. to about 70° C.

12. The method of any one of inventions 1 to 11, wherein the contacting time is about 30 minutes or less.

13. The method of any one of inventions 1 to 11, wherein the contacting time is about 20 minutes or less.

14. The method of any one of inventions 1 to 11, wherein the contacting time is about 10 minutes or less.

15. The method of any one of inventions 1 to 11, wherein the contacting time is about 5 minutes or less.

16. The method of any one of inventions 1 to 15, wherein the hydrophilic polymer are a linear or branched polymer comprising about 25% or less by mole of repeating units of a vinylic monomer having a reactive group of

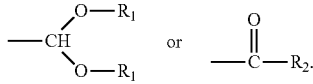

17. The method of any one of inventions 1 to 15, wherein the hydrophilic polymer are a linear or branched polymer comprising about 20% or less by mole of repeating units of a vinylic monomer having a reactive group of

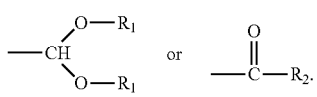

18. The method of any one of inventions 1 to 15, wherein the hydrophilic polymer are a linear or branched polymer comprising about 15% or less by mole of repeating units of a vinylic monomer having a reactive group of

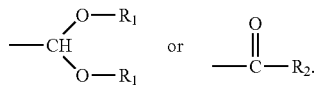

19. The method of any one of inventions 1 to 15, wherein the hydrophilic polymer are a linear or branched polymer comprising about 10% or less by mole of repeating units of a vinylic monomer having a reactive group of

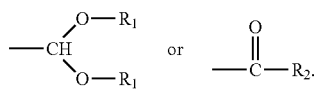

20. The method of any one of inventions 1 to 19, wherein the hydrophilic polymer further comprises repeating units of one or more vinylic monomers selected from the group consisting of a carboxyl-containing vinylic monomer, a primary amine-containing vinylic monomer, a secondary amine-containing vinylic monomer, a non-reactive hydrophilic vinylic monomer, a phosphorylcholine-containing vinylic monomer, and combinations thereof.

21. The method of invention 20, wherein the carboxyl-containing vinylic monomer is selected from the group consisting of acrylic acid, methacrylic ethylacrylic acid, propylacrylic acid, butylacrylic acid, N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carobxy-4-phenyl butadiene-1,3, itaconic acid, citraconic acid, mesaconic acid, glutaconic acid, aconitic acid, maleic acid, fumaric acid, tricarboxy ethylene, and combinations thereof, wherein the primary and secondary amine-containing vinylic monomers are amino-$C_2$-$C_6$ alkyl (meth)acrylate, $C_1$-$C_6$ alkylamino-$C_2$-$C_6$ alkyl (meth)acrylate, allylamine, vinylamine, amino-$C_2$-$C_6$ alkyl (meth)acrylamide, $C_1$-$C_6$ alkylamino-$C_2$-$C_6$ alkyl (meth)acrylamide, or a combination thereof, wherein the non-reactive hydrophilic vinylic monomer is (meth)acrylamide, N,N-dimethyl (meth)acrylamide, N-vinylpyrrolidone (NVP), N-vinyl formamide, N-vinyl acetamide, N-vinyl isopropylamide, N-vinyl-N-methyl acetamide, N,N-dimethylaminoethyl (meth)acrylate, N,N-dimethylaminopropyl (meth)acrylamide, N-2-hydroxylethyl (meth)acrylamide, N,N-bis(hydroxyethyl) (meth)acrylamide, N-3-hydroxypropyl (meth)acrylamide, N-2-hydroxypropyl (meth)acrylamide, N-2,3-dihydroxypropyl (meth)acrylamide, N-tris(hydroxymethyl)methyl (meth)acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, 3-hydroxypropyl (meth)acrylate, 2-hydroxypropyl (meth)acrylate, glycerol (meth)acrylate, $C_1$-$C_4$-alkoxy polyethylene glycol (meth)acrylate having a weight average molecular weight of up to 1500 Daltons, allyl alcohol, vinyl alcohol, or a combination thereof.

22. The method of any one of inventions 1 to 19, wherein the hydrophilic polymer further comprises repeating units of one or more vinylic monomers selected from the group consisting of acryamide, N,N-dimethylacrylamide, N-vinylpyrrolidone, (meth)acryloyloxyethyl phosphorylcholine, N-vinyl-N-methyl acetamide, glycerol (meth)acrylate, hydroxyethyl (meth)acrylate, N-hydroxyethyl (meth)acrylamide, $C_1$-$C_4$-alkoxy polyethylene glycol (meth)acrylate having a weight average molecular weight of up to 400 Daltons, vinyl alcohol, and combinations thereof.

23. The method of any one of inventions 1 to 19, wherein the hydrophilic polymer further comprises repeating units of one or more vinylic monomers selected from the group consisting of a carboxyl-containing vinylic monomer, a primary amine-containing vinylic monomer, a secondary amine-containing vinylic monomer, and combinations thereof.

24. The method of invention 23, wherein the hydrophilic polymer comprises repeating units of one or more carboxyl-containing vinylic monomers selected from the group consisting of acrylic acid, methacrylic acid, ethylacrylic acid, and combinations thereof.

25. The method of invention 23, wherein the hydrophilic polymer comprises repeating units of one or more vinylic monomers selected from the group consisting of amino-$C_2$-$C_3$ alkyl (meth)acrylate, $C_1$-$C_2$ alkylamino-$C_2$-$C_3$ alkyl (meth)acrylate, amino-$C_2$-$C_3$ alkyl (meth)acrylamide, $C_1$-$C_2$ alkylamino-$C_2$-$C_3$ alkyl (meth)acrylamide, and combinations thereof.

26. The method of any one of inventions 23 to 25, wherein the method further comprises a step of heating the pre-formed polyvinylalcohol-based hydrogel contact lens having the layer (or coating) of the hydrophilic polymer thereon in a second aqueous coating solution comprising a water-soluble thermally-crosslinkable polymeric material having azetidinium groups to a temperature of from about 60° C. to about 125° C. and maintaining at the temperature for a time period to form a hydrogel layer (or coating) on top of the layer (or coating) of the hydrophilic polymer.

27. The method of invention 26, wherein the step of heating is performed by autoclaving the soft contact lens precursor immersed in the second aqueous coating solution in a sealed lens package at a temperature of from about 115° C. to about 125° C. for approximately 20-90 minutes, wherein the second aqueous coating solution is a buffered aqueous solution with a pH of from 6.7 to 7.6.

28. The method of invention 26 or 27, wherein the water-soluble thermally-crosslinkable polymeric material comprises
(i) from about 20% to about 95% by weight of first polymer chains derived from a polyamidoamine-epichlorohydrin,
(ii) from about 5% to about 80% by weight of hydrophilic moieties each derived from at least one first hydrophilicity-enhancing agent having at least one reactive functional group selected from the group consisting of amino group, carboxyl group, thiol group, and combination thereof (preferably carboxyl groups), wherein the hydrophilic moieties are covalently attached to the first polymer chains through one or more covalent linkages each formed between one azetitdinium group and one amino, carboxyl or thiol group of the first hydrophilicity-enhancing agent, and
(iii) azetidinium groups which are parts of the first polymer chains or pendant or terminal groups covalently attached to the first polymer chains.

29. The method of invention 26 or 27, wherein the water-soluble thermally-crosslinkable polymeric material comprises
(i) from about 20% to about 95% by weight of first polymer chains derived from a polyamidoamine-epichlorohydrin,
(ii) from about 5% to about 80% by weight of second polymer chains each derived from at least one second hydrophilicity-enhancing agent having at least one reactive functional group selected from the group consisting of amino group, carboxyl group, thiol group, and combination thereof (preferably carboxyl groups), wherein the second polymer chains are covalently attached to the first polymer chains through one or more covalent linkages each formed between one azetitdinium group and one amino, carboxyl or thiol group of the second hydrophilicity-enhancing agent, and
(iii) azetidinium groups which are parts of the first polymer chains or pendant or terminal groups covalently attached to the first polymer chains.

30. The method of invention 26 or 27, wherein the water-soluble thermally-crosslinkable polymeric material comprises
(i) from about 20% to about 95% by weight of first polymer chains derived from a poly(2-oxazoline-co-ethyleneimine)-epichlorohydrin,
(ii) from about 5% to about 80% by weight of hydrophilic moieties each derived from at least one first hydrophilicity-enhancing agent having at least one reactive functional group selected from the group consisting of amino group, carboxyl group, thiol group, and combination thereof (preferably carboxyl groups), wherein the hydrophilic moieties are covalently attached to the first polymer chains through one or more covalent linkages each formed between one azetitdinium group and one amino, carboxyl or thiol group of the first hydrophilicity-enhancing agent, and
(iii) azetidinium groups which are parts of the first polymer chains or pendant or terminal groups covalently attached to the first polymer chains.

31. The method of invention 26 or 27, wherein the water-soluble thermally-crosslinkable polymeric material comprises
(i) from about 20% to about 95% by weight of first polymer chains derived from a poly(2-oxazoline-co-ethyleneimine)-epichlorohydrin,
(ii) from about 5% to about 80% by weight of second polymer chains each derived from at least one second hydrophilicity-enhancing agent having at least one reactive functional group selected from the group consisting of amino group, carboxyl group, thiol group, and combination thereof (preferably carboxyl groups), wherein the second polymer chains are covalently attached to the first polymer chains through one or more covalent linkages each formed between one azetitdinium group and one amino, carboxyl or thiol group of the hydrophilicity-enhancing agent, and
(iii) azetidinium groups which are parts of the first polymer chains or pendant or terminal groups covalently attached to the first polymer chains.

32. The method of any one of inventions 28 or 30, wherein the first hydrophilicity-enhancing agent is a primary amine-containing monosaccharide, a secondary amine-containing monosaccharide, a carboxyl-containing monosaccharide, a thiol-containing monosaccharide, a primary amine-containing disaccharide, a secondary amine-containing disaccharide, a carboxyl-containing disaccharide, a thiol-containing disaccharide, a primary amine-containing oligosaccharide, a secondary amine-containing oligosaccharide, a carboxyl-containing oligosaccharide, a thiol-containing oligosaccharide, or a combination thereof.

33. The method of any one of inventions 29 or 31, wherein the second hydrophilicity-enhancing agent is: a polyethylene glycol having one sole amino, carboxyl or thiol group; a polyethylene glycol with two terminal amino, carboxyl and/or thiol groups; a multi-arm polyethylene glycol with one or more amino, carboxyl and/or thiol groups; a polyethylene glycol dendrimer with one or more amino, carboxyl and/or thiol groups; or a combination thereof.

34. The method of any one of inventions 29 or 31, wherein the second hydrophilicity-enhancing agent is a copolymer which is a polymerization product of a composition comprising (1) about 60% or less by weight of one or more reactive vinylic monomers and (2) one or more non-reactive hydrophilic vinylic monomers.

35. The method of invention 34, wherein said one or more reactive vinylic monomers are selected from the group consisting of acrylic acid, methacrylic ethylacrylic acid, N,N-2-acrylamidoglycolic acid and combinations thereof.

36. The method of invention 34, wherein said one or more reactive vinylic monomers are amino-$C_2$-$C_6$ alkyl (meth)acrylate, $C_1$-$C_6$ alkylamino-$C_2$-$C_6$ alkyl (meth)acrylate, allylamine, vinylamine, amino-$C_2$-$C_6$ alkyl (meth)acrylamide, $C_1$-$C_6$ alkylamino-$C_2$-$C_6$ alkyl (meth)acrylamide, or combinations thereof.

37. The method of any one of inventions 34 to 36, wherein said one or more non-reactive vinylic monomers are selected from the group consisting of (meth)acrylamide, N,N-dimethyl (meth)acrylamide, N-vinylpyrrolidone (NVP), N-vinyl formamide, N-vinyl acetamide, N-vinyl isopropylamide, N-vinyl-N-methyl acetamide, N,N-dimethylaminoethyl (meth)acrylate, N,N-dimethylaminopropyl (meth)acrylamide, glycerol (meth)acrylate, 3-(meth)acryloylamino-1-propanol, N-hydroxyethyl (meth)acrylamide, N-hydroxypropyl (meth)acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, hydroxypropyl (meth)acrylate, $C_1$-$C_4$-alkoxy polyethylene glycol (meth)acrylate having a weight average molecular weight of up to 1500 Daltons, allyl alcohol, vinyl alcohol, and combinations thereof.

38. The method of any one of inventions 34 to 36, wherein said one or more non-reactive vinylic monomers are selected from the group consisting of acryamide, N,N-dimethylacrylamide, N-vinylpyrrolidone, (meth)acryloyloxyethyl phosphorylcholine, N-vinyl-N-methyl acetamide, glycerol (meth)acrylate, hydroxyethyl (meth)acrylate, N-hydroxyethyl (meth)acrylamide, N-2,3-dihydroxypropyl (meth)acrylamide, $C_1$-$C_4$-alkoxy polyethylene glycol (meth)acrylate having a weight average molecular weight of up to 400 Daltons, vinyl alcohol, and combination thereof.

39. The method of any one of inventions 34 to 36, wherein said one or more non-reactive vinylic monomers are phosphorylcholine-containing vinylic monomers.

40. The method of any one of inventions 34 to 36, wherein said one or more non-reactive vinylic monomers are methacryloyloxyethyl phosphorylcholine.

41. The method of any one of inventions 34 to 40, wherein the composition comprises about 50% or less by weight of said one or more reactive vinylic monomers.

42. The method of any one of inventions 34 to 40, wherein the composition comprises from about 0.1% to about 30% by weight of said one or more reactive vinylic monomers.

43. The method of any one of inventions 34 to 40, wherein the composition comprises from about 0.5% to about 20% by weight of said one or more reactive vinylic monomers.

44. The method of any one of inventions 34 to 40, wherein the composition comprises from about 1% to about 15% by weight of said one or more reactive vinylic monomers.

45. The method of invention 29 or 31, wherein the second hydrophilicity-enhancing agent is a primary amine-containing polysaccharide, a secondary amine-containing polysaccharide, a carboxyl-containing polysaccharide, hyaluronic acid, chondroitin sulfate, or a combination thereof.

46. A soft contact lens, comprising: a polyvinylalcohol-based hydrogel lens body; and a coating thereon, wherein the polyvinylalcohol-based hydrogel lens body is composed of a polymer comprising at least 50% by mole of repeating units of vinyl alcohol, wherein the coating comprises a layer of a hydrophilic polymer, wherein the hydrophilic polymer is a linear or branched polymer comprising about 20% or less by mole of repeating units of a vinylic monomer having a reactive group of

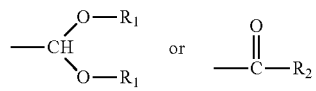

in which R1 is methyl or ethyl and R2 is hydrogen or a $C_1$-$C_4$ alkyl, wherein the layer of the hydrophilic polymer is covalently attached onto the polyvinylalcohol-based hydrogel lens body through 6-membered acetal rings, wherein the soft contact lens has a surface lubricity better than the lubricity of the polyvinylalcohol-based hydrogel lens body.

47. The soft contact lens of invention 46, wherein the hydrophilic polymer further comprises repeating units of one or more vinylic monomers selected from the group consisting of a carboxyl-containing vinylic monomer, a primary amine-containing vinylic monomer, a secondary amine-containing vinylic monomer, a non-reactive hydrophilic vinylic monomer, a phosphorylcholine-containing vinylic monomer, and combinations thereof.

48. The soft contact lens of invention 47, wherein the carboxyl-containing vinylic monomer is selected from the group consisting of acrylic acid, methacrylic ethylacrylic acid, propylacrylic acid, butylacrylic acid, N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carobxy-4-phenyl butadiene-1,3, itaconic acid, citraconic acid, mesaconic acid, glutaconic acid, aconitic acid, maleic acid, fumaric acid, tricarboxy ethylene, and combinations thereof, wherein the primary and secondary amine-containing vinylic monomers are amino-$C_2$-$C_6$ alkyl (meth)acrylate, $C_1$-$C_6$ alkylamino-$C_2$-$C_6$ alkyl (meth)acrylate, allylamine, vinylamine, amino-$C_2$-$C_6$ alkyl (meth)acrylamide, $C_1$-$C_6$ alkylamino-$C_2$-$C_6$ alkyl (meth)acrylamide, or a combination thereof, wherein the non-reactive hydrophilic vinylic monomer is (meth)acrylamide, N,N-dimethyl (meth)acrylamide, N-vinylpyrrolidone (NVP), N-vinyl formamide, N-vinyl acetamide, N-vinyl isopropylamide, N-vinyl-N-methyl acetamide, N,N-dimethylaminoethyl (meth)acrylate, N,N-dimethylaminopropyl (meth)acrylamide, N-2-hydroxylethyl (meth)acrylamide, N,N-bis(hydroxyethyl) (meth)acrylamide, N-3-hydroxypropyl (meth)acrylamide, N-2-hydroxypropyl (meth)acrylamide, N-2,3-dihydroxypropyl (meth)acrylamide, N-tris(hydroxymethyl)methyl (meth)acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, 2-hydroxypropyl (meth)acrylate, 3-hydroxypropyl (meth)acrylate, glycerol (meth)acrylate, $C_1$-$C_4$-alkoxy polyethylene glycol (meth)acrylate having a weight average molecular weight of up to 1500 Daltons, allyl alcohol, vinyl alcohol, or a combination thereof.

49. The soft contact lens of invention 46, wherein the hydrophilic polymer further comprises repeating units of one or more vinylic monomers selected from the group consisting of acrylamide, N,N-dimethylacrylamide, N-vinylpyrrolidone, (meth)acryloyloxyethyl phosphorylcholine, N-vinyl-N-methyl acetamide, glycerol (meth)acrylate, hydroxyethyl (meth)acrylate, N-hydroxyethyl (meth)acrylamide, N-2,3-dihydroxypropyl (meth)acrylamide, $C_1$-$C_4$-alkoxy polyethylene glycol (meth)acrylate having a weight average molecular weight of up to 400 Daltons, vinyl alcohol, and combinations thereof.

50. The soft contact lens of invention 46, wherein the hydrophilic polymer further comprises repeating units of one or more vinylic monomers selected from the group consisting of a carboxyl-containing vinylic monomer, a primary amine-containing vinylic monomer, a secondary amine-containing vinylic monomer, and combinations thereof.

51. The soft contact lens of invention 50, wherein the hydrophilic polymer comprises repeating units of one or more carboxyl-containing vinylic monomers selected from the group consisting of acrylic acid, methacrylic acid, ethylacrylic acid, and combinations thereof.

52. The soft contact lens of invention 50, wherein the hydrophilic polymer comprises repeating units of one or more vinylic monomers selected from the group consisting of amino-$C_2$-$C_3$ alkyl (meth)acrylate, $C_1$-$C_2$ alkylamino-$C_2$-$C_3$ alkyl (meth)acrylate, amino-$C_2$-$C_3$ alkyl (meth)acrylamide, $C_1$-$C_2$ alkylamino-$C_2$-$C_3$ alkyl (meth)acrylamide, and combinations thereof.

53. The soft contact lens of any one of inventions 50 to 52, wherein the coating further comprises a hydrogel layer which is covalently attached onto the layer of the hydrophilic polymer through linkages of

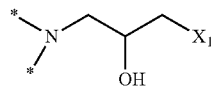

in which $X_1$ is

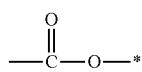

or —NR'—* in which R' is hydrogen or a $C_1$-$C_2$ alkyl group, and * represents an organic radical.

54. The soft contact lens of any one of inventions 46 to 53, wherein the soft contact lens has a water content of preferably from about 15% to about 80%, more preferably from about 30% to about 70% by weight (at room temperature, about 22° C. to 28° C.), when being fully hydrated.

55. The soft contact lens of any one of inventions 46 to 54, wherein the soft contact lens has an elastic modulus of from about 0.2 MPa to about 1.5 MPa (preferably from about 0.3 MPa to about 1.3 MPa, more preferably from about 0.4 MPa to about 1.1 MPa, even more preferably from about 0.5 MPa to about 1.0 MPa), when being fully hydrated.

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

Example 1

Preparation of Poly(Acrylic Acid-co-Acrolein)

Poly(acrylic acid-co-acrolein), poly(AA-co-Ac), was prepared by a thermal radical polymerization of a composition comprising 23.01 g (319 mmol) acrylic acid (Aldrich), 1.99 g (35.5 mmol) acrolein (Aldrich), 0.043 g (0.55 mmol) 2-mercaptoethanol (Aldrich), 0.287 g (0.89 mmol) 2'-Azobis[2-(2-imidazolin-2-yl)propane] dihydrochloride (Wako) and 228 g water at pH=3.0 for 16 h at 44° C. The reaction mixture was diluted to a volume of 500 mL and ultrafiltrated (1 kDa membrane Millipore). After freeze-drying 22.67 g (91%) of a white product with a molecular weight Mw of 74600 Da (GPC: PSS Suprema columns with 100 Å, 1000 Å and 3000 Å pore sizes; PBS solution as eluent; polyacrylic acid as calibration standards) was prepared. $^1$H-NMR (400 MHz, $D_2O$) δ=1.2-2.1 (maxima at 1.65, 1.79, 1.96), 2.47, 2.76, 8.0-9.8 (weak signals), all signals were broad. ATR-FTIR (diamond): ν=795, 1159, 1400, 1449, 1697, 2400-3500, 2600, 2934 and 3000 $cm^{-1}$.

Phosphate Buffered Saline (PBS)

A phosphate buffered saline is prepared by dissolving $NaH_2PO_4$—$H_2O$, $Na_2HPO_4\cdot 2H_2O$, and in a given volume of purified water (distilled or deionized) to have the following composition: about 0.044 w/w % $NaH_2PO4\cdot H_2O$, about 0.388 w/w/% $Na_2HPO_4\cdot 2H_2O$, and about 0.79 w/w % NaCl.

Preparation of Poly(AA-co-Ac) Solution

In a 500 mL flask equipped with a magnetic bar were poured 4.02 g of poly(acrylic acid-co-acrolein) and 396.1 g water (distilled or deionized). This mixture was stirred at ambient temperature until the solid was completely dissolved. Then the solution was acidified to pH=2.0 (controlled with a pH electrode) by addition of a solution of sulfuric acid (25 w/w %; approx. 0.3 mL).

Coating of Polyvinylalcohol-Based Hydrogel Contact Lenses

PVA contact lenses are produced according to an automated lens manufacturing process described in Example 8-8d of WO2002071106 (herein incorporated by reference in its entirety).

PVA contact lenses are dipped into the poly(AA-co-Ac) solution prepared above for 5 minutes at 50° C. and then neutralized in PBS. Finally, the lenses are individually transferred into a polypropylene packaging shell containing 0.65 ml PBS solution, the shell sealed with an Al foil and autoclaved (30 min; 121° C.). Resultant PVA lenses have a layer (or coating) of poly(AA-co-Ac).

Example 2

In-Package-Coating Saline (IPC Saline)

IPC saline comprising a water-soluble thermally-crosslinkable polymeric material is prepared from polyamidoamine-epichlorohydrin (PAE) and poly(acrylamide-co-acrylic acid)(90/10) (i.e., poly(AAm-co-AA) 90/10 as follows.

PAE solutions of different solid contents (Kymene) are purchased from Ashland as an aqueous solution and used as received. Poly(AAm-co-AA)(90/10) partial sodium salt, poly(AAm-co-AA) 90/10, Mw 200,000) is purchased from Polysciences, Inc. and used as received.

The following components: 0.11 w/w % PAE, 0.07 w/w % poly(AAm-co-AA)(90/10), about 0.044 w/w % $NaH_2PO_4.H_2O$, about 0.388 w/w/% $Na_2HPO_4.2H_2O$, and about 0.79 w/w % NaCl, are dissolved in a target amount of purified water (distilled or deionized water) and then pH-adjusted by adding 1 N NaOH to about 7.4. The prepared solution is placed in a container immersed in a water bath. The reaction is carried out at about 65° C. for about 6 hours. Remove the container with the solution therein from the water bath and cool it down by putting it in room temperature water, obtained the IPC saline including a water-soluble thermally-crosslinkable polymeric material. Up to 5 ppm hydrogen peroxide maybe added to the final IPC saline to prevent bioburden growth and the IPC saline is filtered using a 0.22 micron membrane filter.

PVA Lenses with Hydrogel Top Coating

PVA contact lenses with a layer (or coating) of poly(AA-co-Ac), obtained in Example 1, are placed in a packaging shell together with 0.65 ml of the IPC saline prepared above. The shell is sealed with an Al foil and autoclaved at 121° C. for 30 min. Resultant lenses have a top hydrogel coating which is chemically attached onto the layer (or coating) of poly(AA-co-Ac) through linkages each formed between one azetidinium group of PAE modified with poly(AAm-co-AA) and one carboxyl group of poly(AA-co-Ac).

Example 3

Preparation of Poly(Acrylamide-Co-Acrolein)

Poly(acrylamide-co-acrolein), poly(AAm-co-Ac), was prepared by a thermal radical polymerization of a composition comprising 9.19 g (129 mmol) acrylamide, 0.806 g (14.4 mmol) acrolein (Aldrich), 0.035 g (0.45 mmol) 2-mercaptoethanol (Aldrich), 0.116 g (0.36 mmol) 2'-Azobis[2-(2-imidazolin-2-yl)propane] dihydrochloride (Wako) and 91.4 g water for 4 h at 44° C. The reaction mixture was poured into 900 mL ethanol (EtOH) and the resulting precipitate isolated by filtration, again dissolved/precipitated in water/EtOH and isolated and then dried in vacuum (30 mbar) at 30° C. By this method 3.45 g (34.5%) of a white product with a molecular weight Mw of 57900 Da (GPC: PSS Suprema columns with 100 Å, 1000 Å and 3000 Å pore sizes; PBS solution as eluent; polyacrylic acid as calibration standards) was prepared. $^1$H-NMR (400 MHz, D2O) δ=1.2-2.1 (maxima at 1.62, 1.82), 2.1-2.7 (maxima at 2.22, 2.38) all signals were broad.

ATR-FTIR (Diamond): ν=1047, 1084, 1125, 1206, 1282, 1320, 1349, 1415, 1451, 1666, 2932, 3120, 3340 $cm^{-1}$.

Preparation of Poly(AAm-co-Ac) Solution

In a 100 mL flask equipped with a magnetic bar were poured 0.504 g of poly(acrylamide-co-acrolein) and 49.58 g water (distilled or deionized). This mixture was stirred at ambient temperature until the solid was completely dissolved. Then the solution was acidified to pH=2.0 (controlled with a pH electrode) by addition of a solution of hydro chloric acid (6N; approx. 6.0 mL).

Coating of Polyvinylalcohol-Based Hydrogel Contact Lenses

PVA contact lenses are produced according to an automated lens manufacturing process described in Example 8-8d of WO2002071106 (herein incorporated by reference in its entirety). PVA contact lenses are dipped into the poly(AAm-co-Ac) solution prepared above for 5 minutes at 50° C. and then neutralized in PBS. Finally, the lenses are individually transferred into a polypropylene packaging shell containing 0.65 ml PBS solution, the shell sealed with an Al foil and autoclaved (30 min; 121° C.). Resultant PVA lenses have a layer (or coating) of poly(AA-co-Ac).

Example 4

The control experiments are performed with DAILIES® AquaComfort Plus® lenses (Alcon).

Example 5

Water Break-up Time (WBUT) Tests

The surface hydrophilicity of lenses was assessed by determining the time required for the water film to start breaking on the lens surface. Lenses were removed from the packaging shell with tweezers, immersed by shaking for 5 s in a PBS solution, removed from the solution and held against a bright light source. The time that was needed for the water film to break (de-wet) exposing the underlying lens material is noted as WBUT at pH=7. Then the lens was immersed for 5 s in a aqueous solution of hydrochloric acid with pH=2 and the time needed for film beak-up again determined as WBUT at pH=2

Water Contact Angle (WCA) Tests

The measurement was performed by sessile drop method with a DAS 10 drop shape analysis system from Krüss, Germany with pure water (Fluka, surface tension 72.7 mN/M at 20° C.). For measurement purposes a contact lens is taken off the storage solution with tweezers and excess storage solution is removed by gentle shaking of the lens in a PBS solution. The contact lens was placed on the male part of a contact lens mold and gently blotted with a dry and clean cloth. A water droplet (about 1 μL) was then dosed on the lens apex, and the change of contact angle over time of this water droplet (WCA(t), circle fitting mode) was monitored; the WCA at pH=7 was calculated by extrapolation of the graph WCA(t) to t=0. For measuring of the WCA at pH=2 the lens was immersed for 10 s in a aqueous solution with pH=2 (acidified with hydrochloric acid) and the subsequent measuring steps repeated Lubricity Tests The lubricity of a lens was evaluated by using a finger-felt lubricity test which characterizes qualitatively the lubricity of a lens surface on a friction scale from 0 to 4. The higher the friction rating is, the lower the lubricity. Commercial lenses: Dailies® Total 1 ®, Acuvue® TrueEye®, Dailies® AquaComfort Plus® and Air Optix® were assigned friction ratings of 0, 2, 3 and 4.

Before performing the evaluations hands should thoroughly cleaned with a soap solution first and DI water second and dried. The lenses were removed with tweezers from the packaging shells and immersed for 5 s in PBS solution. Then the lenses were placed between the tips of index finger and middle finger and by a gentle rubbing of the lens between them surface lubricity evaluated against the above mentioned standards.

Characterization of Contact Lenses

Lenses from Example 1 are analyzed by ATR-:FTIR. Carboxyl groups are detected on the surfaces of the lenses, indicating that a substantial amount of poly(AA-co-Ac) is anchored to the lens surface, most probably with a concentration gradient from the top into the bulk.

Lenses from example 1 to 4 are investigated regarding water contact angle (WCA) water break-up time (WBUT), lubricity evaluated manually with fingers. The results of these investigations are summarized in Table 1.

TABLE 1

| | | | WCA (°) | | WBUT (s) | |
|---|---|---|---|---|---|---|
| Example | Coating | Lubric-ity* | pH 7.0 | pH 2.0 | pH 7.0 | pH 2.0 |
| 1 | Poly(AA-co-Ac) | 0 | <10 | 30 | >10 | 0 |
| 2 | Poly(AA-co-Ac) + IPC | 0 | 18 | 23 | >10 | >10 |
| 3 | Poly(AAm-co-Ac) | 2 | <10 | 28 | 6 | 3 |
| 4 (control) | NA | 3 | 34 | 28 | >10 | >10 |

The results in Table 1 show that the lubricity of PVA contact lenses can be enhanced significantly by coating them according to a method of the invention.

What is claimed is:

1. A method for producing soft contact lenses, comprising the steps of:
   (1) obtaining a preformed polyvinylalcohol-based hydrogel contact lens, wherein the preformed polyvinylalcohol-based hydrogel contact lens is composed of a polymer comprising at least 50% by mole of repeating units of vinyl alcohol;
   (2) contacting the preformed polyvinylalcohol-based hydrogel contact lens with a first aqueous coating solution of a hydrophilic polymer having reactive groups of

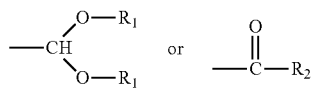

in which $R_1$ is methyl or ethyl and $R_2$ is hydrogen or a $C_1$-$C_4$ alkyl, at a pH of about 4.0 or less for a contacting time to covalently attach a layer of the hydrophilic polymer onto the preformed polyvinylalcohol-based hydrogel contact lens through 6-membered acetal rings.

2. The method of claim 1, wherein the contacting time is about 30 minutes or less, wherein the first aqueous coating solution has a temperature of from about 35° C. to about 85° C.

3. The method of claim 2, wherein the hydrophilic polymer are a linear or branched polymer comprising about 25% or less by mole of repeating units of a vinylic monomer having a reactive group of

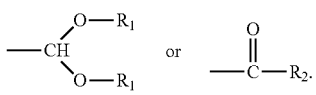

4. The method of claim 3, wherein the hydrophilic polymer further comprises repeating units of one or more vinylic monomers selected from the group consisting of a carboxyl-containing vinylic monomer, a primary amine-containing vinylic monomer, a secondary amine-containing vinylic monomer, a non-reactive hydrophilic vinylic monomer, a phosphorylcholine-containing vinylic monomer, and combinations thereof.

5. The method of claim 4, wherein the carboxyl-containing vinylic monomer is selected from the group consisting of acrylic acid, methacrylic ethylacrylic acid, propylacrylic acid, butylacrylic acid, N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carobxy-4-phenyl butadiene-1,3, itaconic acid, citraconic acid, mesaconic acid, glutaconic acid, aconitic acid, maleic acid, fumaric acid, tricarboxy ethylene, and combinations thereof,
   wherein the primary and secondary amine-containing vinylic monomers are amino-$C_2$-$C_6$ alkyl (meth)acrylate, $C_1$-$C_6$ alkylamino-$C_2$-$C_6$ alkyl (meth)acrylate, allylamine, vinylamine, amino-$C_2$-$C_6$ alkyl (meth)acrylamide, $C_1$-$C_6$ alkylamino-$C_2$-$C_6$ alkyl (meth)acrylamide, or a combination thereof,
   wherein the non-reactive hydrophilic vinylic monomer is (meth)acrylamide, N,N-dimethyl (meth)acrylamide, N-vinylpyrrolidone (NVP), N-vinyl formamide, N-vinyl acetamide, N-vinyl isopropylamide, N-vinyl-N-methyl acetamide, N,N-dimethylaminoethyl (meth)acrylate, N,N-dimethylaminopropyl (meth)acrylamide, N-2-hydroxylethyl (meth)acrylamide, N,N-bis(hydroxyethyl) (meth)acrylamide, N-3-hydroxypropyl (meth)acrylamide, N-2-hydroxypropyl (meth)acrylamide, N-2,3-dihydroxypropyl (meth)acrylamide, N-tris(hydroxymethyl)methyl (meth)acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, 2-hydroxypropyl (meth)acrylate, 3-hydroxypropyl (meth)acrylate, glycerol (meth)acrylate, $C_1$-$C_4$-alkoxy polyethylene glycol (meth)acrylate having a weight average molecular weight of up to 1500 Daltons, allyl alcohol, vinyl alcohol, or a combination thereof.

6. The method of claim 4, wherein the hydrophilic polymer comprises repeating units of one or more vinylic monomers selected from the group consisting of a phosphorylcholine-containing vinylic monomer, (meth)acrylamide, N,N-dimethyl (meth)acrylamide, N-vinylpyrrolidone (NVP), N-vinyl formamide, N-vinyl acetamide, N-vinyl isopropylamide, N-vinyl-N-methyl acetamide, N,N-dimethylaminoethyl (meth)acrylate, N,N-dimethylaminopropyl (meth)acrylamide, N-2-hydroxylethyl (meth)acrylamide, N,N-bis(hydroxyethyl) (meth)acrylamide, N-3-hydroxypropyl (meth)acrylamide, N-2-hydroxypropyl (meth)acrylamide, N-2,3-dihydroxypropyl (meth)acrylamide, N-tris(hydroxymethyl)methyl (meth)acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, 2-hydroxypropyl (meth)acrylate, 3-hydroxypropyl (meth)acrylate, glycerol (meth)acrylate, $C_1$-$C_4$-alkoxy polyethylene glycol (meth)acrylate having a weight average molecular weight of up to 1500 Daltons, allyl alcohol, vinyl alcohol, or a combination thereof.

7. The method of claim 4, wherein the hydrophilic polymer comprises repeating units of one or more carboxyl-containing vinylic monomers selected from the group consisting of acrylic acid, methacrylic acid, ethylacrylic acid, and combinations thereof.

8. The method of claim 4, wherein the hydrophilic polymer comprises repeating units of one or more vinylic monomers selected from the group consisting of amino-$C_2$-$C_3$ alkyl (meth)acrylate, $C_1$-$C_2$ alkylamino-$C_2$-$C_3$ alkyl (meth)acrylate, amino-$C_2$-$C_3$ alkyl (meth)acrylamide, $C_1$-$C_2$ alkylamino-$C_2$-$C_3$ alkyl (meth)acrylamide, and combinations thereof.

9. The method of claim 4, wherein the method further comprises a step of heating the preformed polyvinylalcohol-based hydrogel contact lens having the layer (or coating) of the hydrophilic polymer thereon in a second aqueous coating solution comprising a water-soluble thermally-crosslinkable polymeric material having azetidinium groups to a temperature of from about 60° C. to about 125° C. and maintaining at the temperature for a time period to form a hydrogel layer (or coating) on top of the layer (or coating) of the hydrophilic polymer.

10. The method of claim 9, wherein the step of heating is performed by autoclaving the soft contact lens precursor immersed in the second aqueous coating solution in a sealed lens package at a temperature of from about 115° C. to about 125° C. for approximately 20-90 minutes, wherein the second aqueous coating solution is a buffered aqueous solution with a pH of from 6.7 to 7.6.

11. The method of claim 10, wherein the water-soluble thermally-crosslinkable polymeric material comprises (i) from about 20% to about 95% by weight of first polymer chains derived from a polyamidoamine-epichlorohydrin and/or a poly(2-oxazoline-co-ethyleneimine)-epichlorohydrin, (ii) from about 5% to about 80% by weight of hydrophilic moieties and/or second polymer chains, wherein each of the hydrophilic moieties is derived from at least one first hydrophilicity-enhancing agent having at least one reactive functional group selected from the group consisting of amino group, carboxyl group, thiol group, and combination thereof, wherein the hydrophilic moieties are covalently attached to the first polymer chains through one or more covalent linkages each formed between one azetitdinium group and one amino, carboxyl or thiol group of the first hydrophilicity-enhancing agent, wherein each of the second polymer chains is derived from at least one second hydrophilicity-enhancing agent having at least one reactive functional group selected from the group consisting of amino group, carboxyl group, thiol group, and combination thereof, wherein the second polymer chains are covalently attached to the first polymer chains through one or more covalent linkages each formed between one azetitdinium group and one amino, carboxyl or thiol group of the second hydrophilicity-enhancing agent, and (iii) azetidinium groups which are parts of the first polymer chains or pendant or terminal groups covalently attached to the first polymer chains.

12. The method of claim 11, wherein the first hydrophilicity-enhancing agent is a primary amine-containing monosaccharide, a secondary amine-containing monosaccharide, a carboxyl-containing monosaccharide, a thiol-containing monosaccharide, a primary amine-containing disaccharide, a secondary amine-containing disaccharide, a carboxyl-containing disaccharide, a thiol-containing disaccharide, a primary amine-containing oligosaccharide, a secondary amine-containing oligosaccharide, a carboxyl-containing oligosaccharide, a thiol-containing oligosaccharide, or a combination thereof.

13. The method of claim 11, wherein the second hydrophilicity-enhancing agent is:

a polyethylene glycol having one sole amino, carboxyl or thiol group;
a polyethylene glycol with two terminal amino, carboxyl and/or thiol groups;
a multi-arm polyethylene glycol with one or more amino, carboxyl and/or thiol groups;
a polyethylene glycol dendrimer with one or more amino, carboxyl and/or thiol groups;
a copolymer which is a polymerization product of a composition comprising (1) about 60% or less by weight of one or more reactive vinylic monomers selected from the group consisting of acrylic acid, methacrylic ethylacrylic acid, N,N-2-acrylamidoglycolic acid and combinations thereof and (2) one or more non-reactive hydrophilic vinylic monomers;
a copolymer which is a polymerization product of a composition comprising (1) about 60% or less by weight of one or more reactive vinylic monomers selected from the group consisting of amino-$C_2$-$C_6$ alkyl (meth)acrylate, $C_1$-$C_6$ alkylamino-$C_2$-$C_6$ alkyl (meth)acrylate, allylamine, vinylamine, amino-$C_2$-$C_6$ alkyl (meth)acrylamide, $C_1$-$C_6$ alkylamino-$C_2$-$C_6$ alkyl (meth)acrylamide, and combinations thereof and (2) one or more non-reactive hydrophilic vinylic monomers;
a primary amine-containing polysaccharide;
a secondary amine-containing polysaccharide;
a carboxyl-containing polysaccharide;
hyaluronic acid;
chondroitin sulfate; or
a combination thereof,
wherein said one or more non-reactive hydrophilic vinylic monomers are selected from the group consisting of a phosphorylcholine-containing vinylic monomer, (meth)acrylamide, N,N-dimethyl (meth)acrylamide, N-vinylpyrrolidone (NVP), N-vinyl formamide, N-vinyl acetamide, N-vinyl isopropylamide, N-vinyl-N-methyl acetamide, N,N-dimethylaminoethyl (meth)acrylate, N,N-dimethylaminopropyl (meth)acrylamide, N-2-hydroxylethyl (meth)acrylamide, N,N-bis(hydroxyethyl) (meth)acrylamide, N-3-hydroxypropyl (meth)acrylamide, N-2-hydroxypropyl (meth)acrylamide, N-2,3-dihydroxypropyl (meth)acrylamide, N-tris (hydroxymethyl)methyl (meth)acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, 2-hydroxypropyl (meth)acrylate, 3-hydroxypropyl (meth)acrylate, glycerol (meth)acrylate, $C_1$-$C_4$-alkoxy polyethylene glycol (meth)acrylate having a weight average molecular weight of up to 1500 Daltons, allyl alcohol, vinyl alcohol, and combinations thereof.

14. A soft contact lens, comprising: a polyvinylalcohol-based hydrogel lens body; and a coating thereon, wherein the polyvinylalcohol-based hydrogel lens body is composed of a polymer comprising at least 50% by mole of repeating units of vinyl alcohol, wherein the coating comprises a layer of a hydrophilic polymer, wherein the hydrophilic polymer is a linear or branched polymer comprising about 20% or less by mole of repeating units of a vinylic monomer having a reactive group of

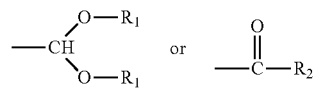

in which $R_1$ is methyl or ethyl and $R_2$ is hydrogen or a $C_1$-$C_4$ alkyl, wherein the layer of the hydrophilic polymer is covalently attached onto the polyvinylalcohol-based hydrogel lens body through 6-membered acetal rings, wherein the soft contact lens has a surface lubricity better than the lubricity of the polyvinylalcohol-based hydrogel lens body.

15. The soft contact lens of claim 14, wherein the hydrophilic polymer are a linear or branched polymer comprising about 25% or less by mole of repeating units of a vinylic monomer having a reactive group of

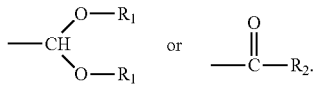

16. The soft contact lens of claim 14, wherein the hydrophilic polymer further comprises repeating units of one or more vinylic monomers selected from the group consisting of a carboxyl-containing vinylic monomer, a primary amine-containing vinylic monomer, a secondary amine-containing vinylic monomer, a non-reactive hydrophilic vinylic monomer, a phosphorylcholine-containing vinylic monomer, and combinations thereof.

17. The soft contact lens of claim 16, wherein the hydrophilic polymer comprises repeating units of one or more vinylic monomers selected from the group consisting of (meth)acrylamide, N,N-dimethyl (meth)acrylamide, N-vinylpyrrolidone (NVP), N-vinyl formamide, N-vinyl acetamide, N-vinyl isopropylamide, N-vinyl-N-methyl acetamide, N,N-dimethylaminoethyl (meth)acrylate, N,N-dimethylaminopropyl (meth)acrylamide, N-2-hydroxylethyl (meth)acrylamide, N,N-bis(hydroxyethyl) (meth)acrylamide, N-3-hydroxypropyl (meth)acrylamide, N-2-hydroxypropyl (meth)acrylamide, N-2,3-dihydroxypropyl (meth)acrylamide, N-tris(hydroxymethyl)methyl (meth)acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 2-hydroxyethyl (meth)acrylate, 2-hydroxypropyl (meth)acrylate, 3-hydroxypropyl (meth)acrylate, glycerol (meth)acrylate, $C_1$-$C_4$-alkoxy polyethylene glycol (meth)acrylate having a weight average molecular weight of up to 1500 Daltons, allyl alcohol, vinyl alcohol, or a combination thereof.

18. The soft contact lens of claim 14, wherein the coating further comprises a hydrogel layer which is covalently attached onto the layer of the hydrophilic polymer through linkages of

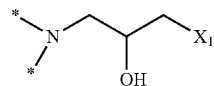

in which $X_1$ is

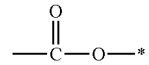

or —NR'—* in which R' is hydrogen or a $C_1$-$C_2$ alkyl group, and * represents an organic radical.

19. The soft contact lens of claim 17, wherein the soft contact lens has a water content of from about 15% to about 80% by weight (at room temperature, about 22° C. to 28° C.), and an elastic modulus of from about 0.2 MPa to about 1.5 MPa, when being fully hydrated.

20. The soft contact lens of claim 18, wherein the soft contact lens has a water content of from about 15% to about 80% by weight (at room temperature, about 22° C. to 28° C.), and an elastic modulus of from about 0.2 MPa to about 1.5 MPa, when being fully hydrated.

* * * * *